(12) United States Patent
Justis et al.

(10) Patent No.: US 7,833,252 B2
(45) Date of Patent: Nov. 16, 2010

(54) PIVOTING JOINTS FOR SPINAL IMPLANTS INCLUDING DESIGNED RESISTANCE TO MOTION AND METHODS OF USE

(75) Inventors: Jeff R. Justis, Germantown, TN (US); Fred J. Molz, IV, Birmingham, AL (US); James Michael Mirda, Cordova, TN (US); Rodney Ray Ballard, Lakeland, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 978 days.

(21) Appl. No.: 11/493,447

(22) Filed: Jul. 26, 2006

(65) Prior Publication Data

US 2007/0233078 A1 Oct. 4, 2007

Related U.S. Application Data

(63) Continuation-in-part of application No. 11/341,188, filed on Jan. 27, 2006.

(51) Int. Cl.
*A61B 17/88* (2006.01)
*A61B 17/70* (2006.01)
*A61B 17/04* (2006.01)

(52) U.S. Cl. .................. 606/279; 606/269; 606/306; 606/308

(58) Field of Classification Search .......... 606/279, 606/264–270, 305, 306, 308
See application file for complete search history.

(56) References Cited

U.S. PATENT DOCUMENTS

| 4,304,011 | A | 12/1981 | Whelan, II |
| 4,946,458 | A | 8/1990 | Harms et al. |
| 5,084,048 | A | 1/1992 | Jacob et al. |
| 5,190,543 | A | 3/1993 | Schlapfer |

(Continued)

FOREIGN PATENT DOCUMENTS

WO 2005004699 A2 1/2005

(Continued)

OTHER PUBLICATIONS

Orbitform Group, LLC, "What is Orbit Forming." *Orbitform: Maufacturer of Orbital Forming, Fastening, Riveting, Assembly, Heat Sinking Systems and . . .* , Jun. 1, 2007, 2 pages, http://www.orbitform.com/riveting/what_is_orbital_forming.htm.

(Continued)

*Primary Examiner*—Eduardo C Robert
*Assistant Examiner*—Ellen C Hammond

(57) ABSTRACT

A pivoting connector couples a vertebral member to a longitudinal member. An anchor is pivotally attached to a body by positioning a head of the anchor within a cavity in the body. A longitudinal rod is inserted into a channel also positioned within the body and axially aligned with the cavity. A retainer applies a force to maintain the longitudinal rod within the channel, however the force may be isolated from the anchor. One embodiment may include a compression member that is separate from or integral with the body. The compression member may transmit a rod securing force to the anchor to secure or limit the pivoting movement of the anchor member relative to the body. The compression member may deflect or detach under the influence of the securing force.

9 Claims, 16 Drawing Sheets

U.S. PATENT DOCUMENTS

| | | |
|---|---|---|
| 5,443,467 A | 8/1995 | Biedermann et al. |
| 5,474,555 A | 12/1995 | Puno et al. |
| 5,480,041 A | 1/1996 | Turner |
| 5,549,608 A | 8/1996 | Errico et al. |
| 5,591,166 A | 1/1997 | Bernhardt et al. |
| 5,669,911 A | 9/1997 | Errico et al. |
| 5,728,098 A * | 3/1998 | Sherman et al. .............. 606/269 |
| 5,733,285 A | 3/1998 | Errico et al. |
| 5,797,911 A | 8/1998 | Sherman et al. |
| 5,810,819 A | 9/1998 | Errico et al. |
| 5,817,094 A | 10/1998 | Errico et al. |
| 5,863,293 A | 1/1999 | Richelsoph |
| 5,882,350 A | 3/1999 | Ralph et al. |
| 5,885,286 A | 3/1999 | Sherman et al. |
| 5,888,204 A | 3/1999 | Ralph et al. |
| 5,954,725 A * | 9/1999 | Sherman et al. ............... 606/78 |
| 5,989,254 A | 11/1999 | Katz |
| 6,063,090 A | 5/2000 | Schlapfer |
| 6,074,391 A | 6/2000 | Metz-Stavenhagen et al. |
| 6,082,923 A * | 7/2000 | Maughan .................... 403/135 |
| 6,132,434 A * | 10/2000 | Sherman et al. ............... 606/78 |
| 6,146,421 A | 11/2000 | Gordon et al. |
| 6,258,089 B1 | 7/2001 | Campbell et al. |
| 6,261,287 B1 | 7/2001 | Metz-Stavenhagen |
| 6,280,442 B1* | 8/2001 | Barker et al. .................. 606/60 |
| 6,287,311 B1* | 9/2001 | Sherman et al. ............... 606/78 |
| 6,290,703 B1 | 9/2001 | Ganem |
| RE37,665 E | 4/2002 | Ralph et al. |
| 6,440,137 B1 | 8/2002 | Horvath et al. |
| 6,454,773 B1* | 9/2002 | Sherman et al. ............... 606/78 |
| 6,537,276 B2 | 3/2003 | Metz-Stavenhagen |
| 6,554,834 B1 | 4/2003 | Crozet et al. |
| 6,605,090 B1 | 8/2003 | Trieu et al. |
| 6,626,907 B2 | 9/2003 | Campbell et al. |
| 6,626,908 B2 | 9/2003 | Cooper et al. |
| 6,716,214 B1 | 4/2004 | Jackson |
| 6,733,502 B2 | 5/2004 | Altarac et al. |
| 6,736,820 B2 | 5/2004 | Biedermann et al. |
| 6,749,361 B2 | 6/2004 | Hermann et al. |
| 6,793,658 B2 | 9/2004 | LeHuec et al. |
| 6,869,433 B2 | 3/2005 | Glascott |
| 6,918,911 B2 | 7/2005 | Biedermann et al. |
| 6,945,972 B2 | 9/2005 | Frigg et al. |
| 6,964,666 B2 | 11/2005 | Jackson |
| 6,974,460 B2 | 12/2005 | Carbone et al. |
| 6,974,461 B1 | 12/2005 | Wolter |
| 6,991,632 B2 | 1/2006 | Ritland |
| 7,022,122 B2 | 4/2006 | Amrein et al. |
| 7,060,067 B2 | 6/2006 | Needham et al. |
| 7,066,937 B2 | 6/2006 | Shluzas |
| 7,081,116 B1 | 7/2006 | Carly |
| 7,081,117 B2 | 7/2006 | Bono et al. |
| 7,087,057 B2 | 8/2006 | Konieczynski et al. |
| 7,090,674 B2 | 8/2006 | Doubler et al. |
| 7,121,755 B2 | 10/2006 | Schlapfer et al. |
| 7,128,743 B2 | 10/2006 | Metz-Stavenhagen |
| 7,141,051 B2 | 11/2006 | Janowski et al. |
| 7,144,396 B2 | 12/2006 | Shluzas |
| 7,163,539 B2 | 1/2007 | Abdelgany et al. |
| 7,166,109 B2 | 1/2007 | Biedermann et al. |
| 7,179,261 B2 | 2/2007 | Sicvol et al. |
| 7,186,255 B2 | 3/2007 | Baynham et al. |
| 7,195,632 B2 | 3/2007 | Biedermann et al. |
| 7,214,227 B2 | 5/2007 | Colleran et al. |
| 7,223,268 B2 | 5/2007 | Biedermann |
| 7,338,491 B2* | 3/2008 | Baker et al. .................. 606/308 |
| 7,530,992 B2* | 5/2009 | Biedermann et al. ......... 606/272 |
| 7,699,876 B2* | 4/2010 | Barry et al. .................. 606/266 |
| 2002/0138076 A1 | 9/2002 | Biedermann et al. |
| 2003/0045879 A1 | 3/2003 | Minfelde et al. |
| 2004/0049272 A1 | 3/2004 | Reiley |
| 2004/0176766 A1 | 9/2004 | Shluzas |
| 2004/0181224 A1 | 9/2004 | Biedermann et al. |
| 2004/0186473 A1 | 9/2004 | Cournoyer et al. |
| 2004/0225289 A1 | 11/2004 | Biedermann et al. |
| 2004/0249380 A1 | 12/2004 | Glascott |
| 2004/0260284 A1 | 12/2004 | Parker |
| 2004/0267264 A1 | 12/2004 | Konieczynski et al. |
| 2005/0033431 A1 | 2/2005 | Gordon et al. |
| 2005/0033432 A1 | 2/2005 | Gordon et al. |
| 2005/0033439 A1 | 2/2005 | Gordon et al. |
| 2005/0049588 A1 | 3/2005 | Jackson |
| 2005/0049589 A1 | 3/2005 | Jackson |
| 2005/0187548 A1 | 8/2005 | Butler et al. |
| 2005/0192571 A1 | 9/2005 | Abdelgany |
| 2005/0203516 A1 | 9/2005 | Biedermann et al. |
| 2005/0209698 A1 | 9/2005 | Gordon et al. |
| 2005/0228385 A1 | 10/2005 | Iott et al. |
| 2005/0267472 A1 | 12/2005 | Biedermann et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0277919 A1 | 12/2005 | Silvka et al. |
| 2005/0277928 A1 | 12/2005 | Boschert et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2005/0288668 A1 | 12/2005 | Brinkhaus |
| 2006/0084979 A1 | 4/2006 | Jackson |
| 2006/0161152 A1 | 7/2006 | Ensign et al. |
| 2006/0173454 A1 | 8/2006 | Spitler et al. |
| 2006/0195098 A1 | 8/2006 | Schumacher |
| 2006/0200128 A1 | 9/2006 | Mueller |
| 2006/0200131 A1 | 9/2006 | Chao et al. |
| 2006/0200133 A1 | 9/2006 | Jackson |
| 2006/0200136 A1 | 9/2006 | Jackson |
| 2006/0217713 A1 | 9/2006 | Serhan et al. |
| 2006/0217714 A1 | 9/2006 | Serhan et al. |
| 2006/0217715 A1 | 9/2006 | Serhan et al. |
| 2006/0217716 A1 | 9/2006 | Baker et al. |
| 2006/0229616 A1 | 10/2006 | Albert et al. |
| 2006/0235385 A1 | 10/2006 | Whipple |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241599 A1 | 10/2006 | Konieczynski et al. |
| 2006/0241600 A1 | 10/2006 | Ensign et al. |
| 2006/0241603 A1 | 10/2006 | Jackson |
| 2006/0241769 A1 | 10/2006 | Gordon et al. |
| 2006/0241771 A1 | 10/2006 | Gordon et al. |
| 2006/0247631 A1 | 11/2006 | Ahn et al. |
| 2006/0247636 A1 | 11/2006 | Yuan et al. |
| 2006/0264933 A1 | 11/2006 | Baker et al. |
| 2006/0271047 A1 | 11/2006 | Jackson |
| 2006/0271053 A1 | 11/2006 | Schlapfer et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0293659 A1 | 12/2006 | Alvarez |
| 2006/0293664 A1 | 12/2006 | Schumacher |
| 2006/0293665 A1 | 12/2006 | Shluzas |
| 2006/0293666 A1 | 12/2006 | Matthis et al. |
| 2007/0016198 A1 | 1/2007 | Boehm et al. |
| 2007/0016199 A1 | 1/2007 | Boehm et al. |
| 2007/0016200 A1 | 1/2007 | Jackson |
| 2007/0021750 A1 | 1/2007 | Shluzas et al. |
| 2007/0043355 A1 | 2/2007 | Bette et al. |
| 2007/0043357 A1 | 2/2007 | Kirschman |
| 2007/0043358 A1 | 2/2007 | Molz et al. |
| 2007/0043364 A1 | 2/2007 | Cawley et al. |
| 2007/0049933 A1 | 3/2007 | Ahn et al. |

| | | |
|---|---|---|
| 2007/0055235 A1 | 3/2007 | Janowski et al. |
| 2007/0055238 A1 | 3/2007 | Biedermann et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0073291 A1 | 3/2007 | Cordaro et al. |
| 2007/0078460 A1 | 4/2007 | Frigg et al. |
| 2007/0083199 A1 | 4/2007 | Baccelli |
| 2007/0088357 A1 | 4/2007 | Johnson et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093821 A1 | 4/2007 | Freudiger |
| 2007/0093826 A1 | 4/2007 | Hawkes et al. |
| 2007/0093827 A1 | 4/2007 | Warnick |
| 2007/0093829 A1 | 4/2007 | Abdou |
| 2007/0093831 A1 | 4/2007 | Abdelgany et al. |
| 2007/0093832 A1 | 4/2007 | Abdelgany |
| 2007/0100341 A1 | 5/2007 | Reglos et al. |
| 2007/0106383 A1 | 5/2007 | Abdou |
| 2007/0118117 A1 | 5/2007 | Altarac et al. |
| 2007/0118118 A1 | 5/2007 | Kwak et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123867 A1 | 5/2007 | Kirschman |
| 2007/0123870 A1 | 5/2007 | Jeon et al. |
| 2007/0191839 A1 | 8/2007 | Justis et al. |

FOREIGN PATENT DOCUMENTS

WO    WO 2005/016194 A2    2/2005

OTHER PUBLICATIONS

Orbitform Group, LLC, "What is Rollerforming." *Orbitform: Maufacturer of Orbital Forming, Fastening, Riveting, Assembly, Heat Sinking Systems and . . .* , Jun. 1, 2007, 2 pages, http://www.orbitform.com/products/orbitform/Rollerform_Heads.htm.

* cited by examiner

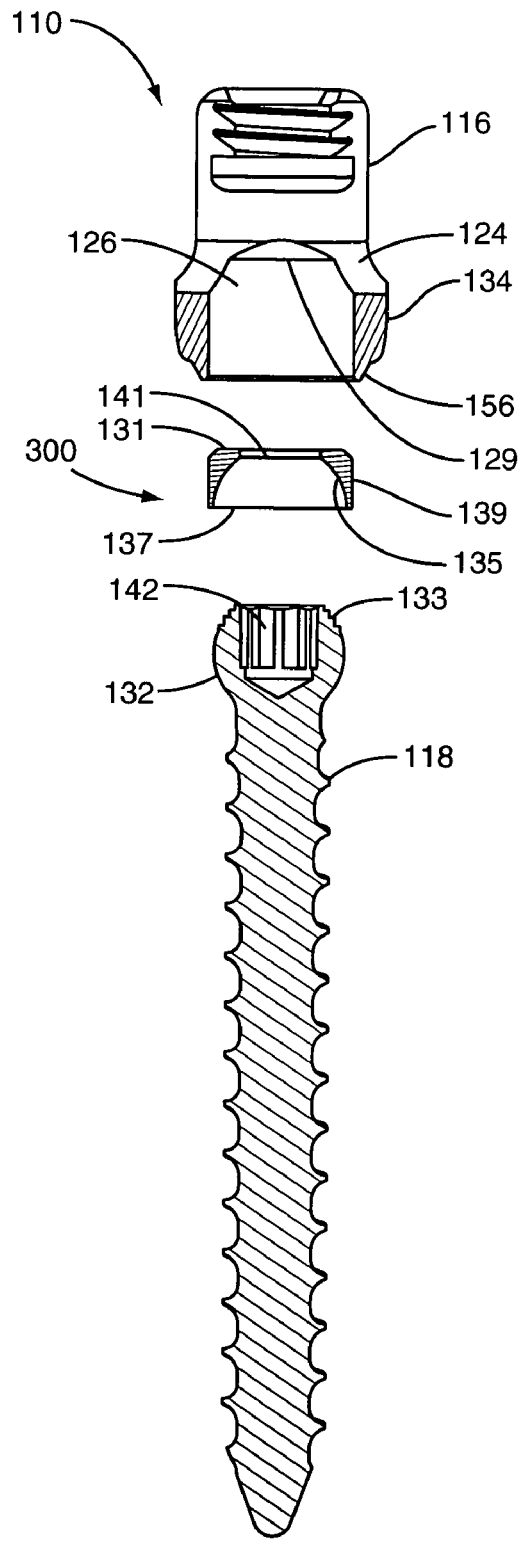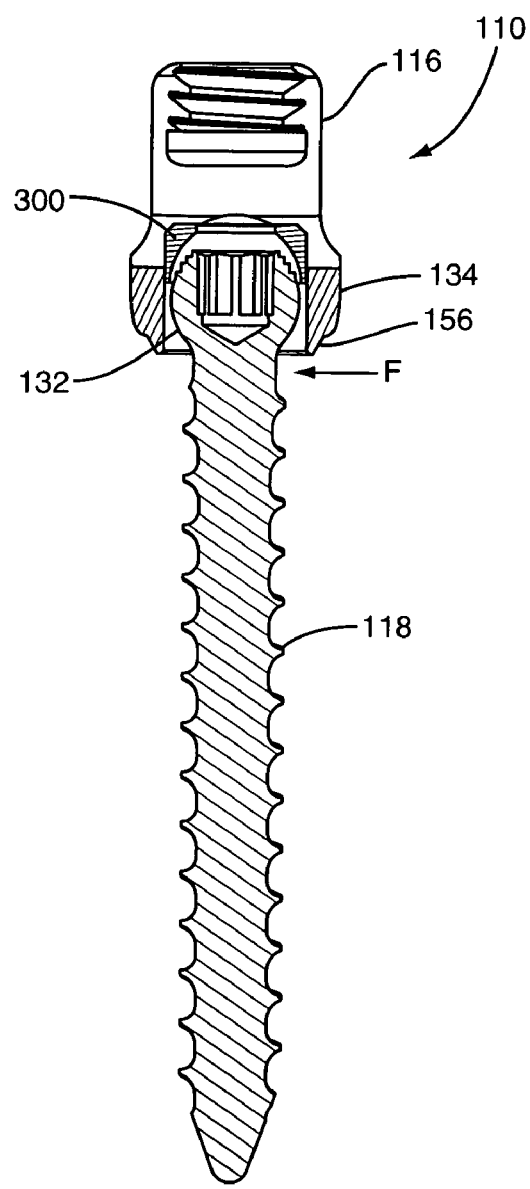
*FIG. 22A*  *FIG. 22B*

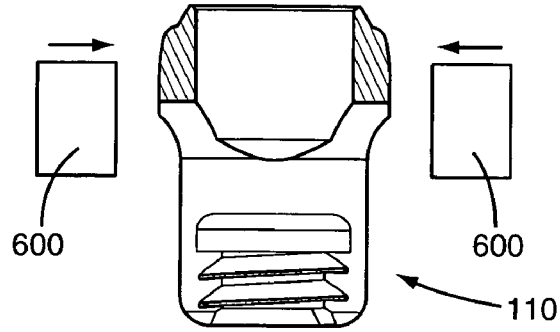
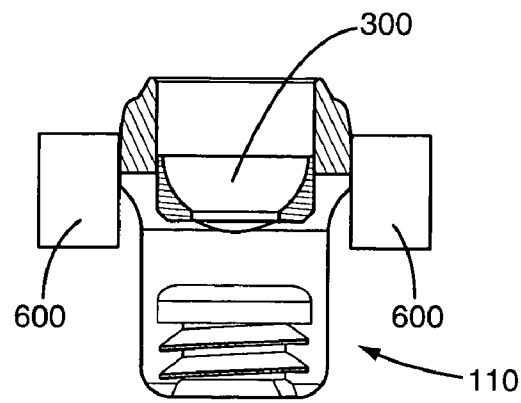
FIG. 28A  FIG. 28B
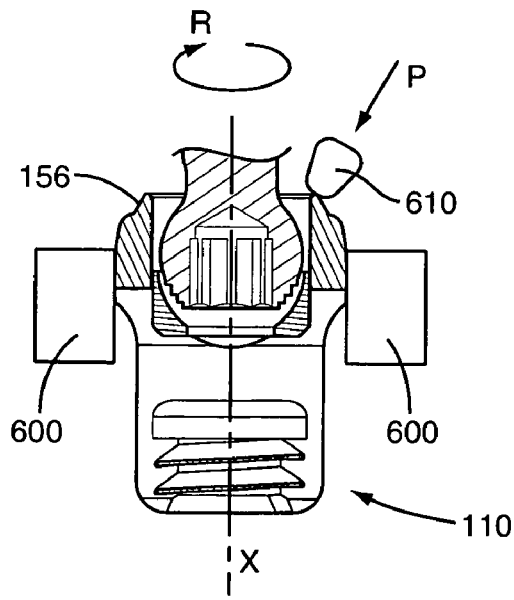
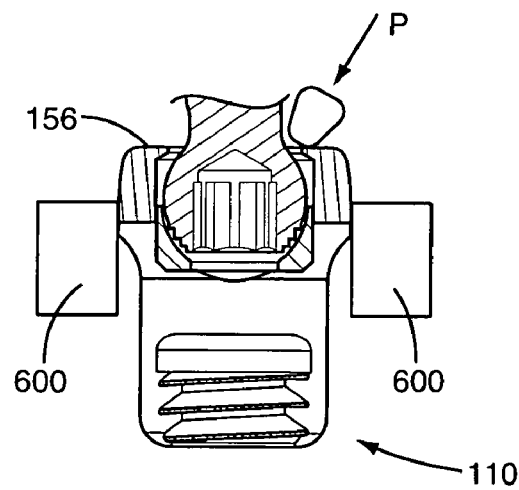
FIG. 28C  FIG. 28D

PIVOTING JOINTS FOR SPINAL IMPLANTS INCLUDING DESIGNED RESISTANCE TO MOTION AND METHODS OF USE

This application is a Continuation-In-Part of U.S. patent application Ser. No. 11/341,188, filed Jan. 27, 2006.

BACKGROUND

Longitudinal members, such as spinal rods, are often used in the surgical treatment of spinal disorders such as degenerative disc disease, disc herniations, scoliosis or other curvature abnormalities, and fractures. Different types of surgical treatments are used. In some cases, spinal fusion is indicated to inhibit relative motion between vertebral bodies. In other cases, dynamic implants are used to preserve motion between vertebral bodies. For either type of surgical treatment, longitudinal members may be attached to the exterior of two or more vertebrae, whether it is at a posterior, anterior, or lateral side of the vertebrae. In other embodiments, longitudinal members are attached to the vertebrae without the use of dynamic implants or spinal fusion.

Longitudinal members may provide a stable, rigid column that encourages bones to fuse after spinal-fusion surgery. Further, the longitudinal members may redirect stresses over a wider area away from a damaged or defective region. Also, rigid longitudinal members may restore the spine to its proper alignment. In some cases, flexible longitudinal members may be appropriate. Flexible longitudinal members may provide other advantages, such as increasing loading on interbody constructs, decreasing stress transfer to adjacent vertebral elements while bone-graft healing takes place, and generally balancing strength with flexibility.

Conventionally, longitudinal members are secured to vertebral members using rigid clamping devices. These clamping devices may be multi-axial in the sense that they are adjustable prior to securing. However, once secured, the clamping devices are locked in place. A surgeon may wish to implant a flexible rod system and have more freedom to control pivot points or the nature of the pivoting motion. At present, a surgeon might only have a choice between rigid and flexible longitudinal members, which may not necessarily provide the desired degree of flexibility.

SUMMARY

Illustrative embodiments disclosed herein are directed to a pivoting connector that couples a vertebral member to a longitudinal member. An anchor is pivotally attaching to a body by positioning a head of the anchor within a cavity in the body. The body may also include a channel that is also positioned within the body and axially aligned with the cavity. The channel may be disposed on an opposite side of the cavity. An intermediate section may separate the channel and cavity. A longitudinal member may be placed within the channel and a retainer applies a force to maintain the longitudinal rod within the channel. The retaining force applied to the longitudinal member may be isolated from the anchor. The cavity may be adjustable between a plurality of sizes that apply different resistances to pivoting movement of the anchor relative to the body. The adjustment may be performed before or during a surgical procedure. According to one or more embodiment, inserting different components into the cavity may achieve the varying rotational resistances. According to one or more embodiments, rotating a threaded element into or onto the body may create more or less rotational interference or rotational resistance.

The pivoting connector may include a compression element contained within the cavity and forming a receiving area to accommodate the head of the anchor. The compression element may extend into the channel to contact the longitudinal member so that the longitudinal member displaces the compression element into contact with the anchor head when the longitudinal member is secured in the channel. The body may include a deformable sidewall that is moveable between a first state in which the fastener is insertable into the cavity and a second state in which the compression element and the fastener are retained in the cavity. The compression element may be a distinct member or may be formed as a part of the body. In the latter implementation, the compression element may be elastically deformable, plastically deformable, or detachable from the body when displaced into contact with the anchor head by the longitudinal member.

BRIEF DESCRIPTION OF THE DRAWINGS

FIG. 15 is a detailed section view of an interference snap ring that may be used with the pivoting head according to one embodiment;

FIGS. 22A and 22B, respectively, are exploded and unexploded side section views of a pivoting head with a crown member inserted therein according to one embodiment;

FIGS. 28A-D illustrate exemplary process steps by which a crown member and anchor head may be retained within a pivoting head according to one embodiment.

DETAILED DESCRIPTION

Figure 1A:
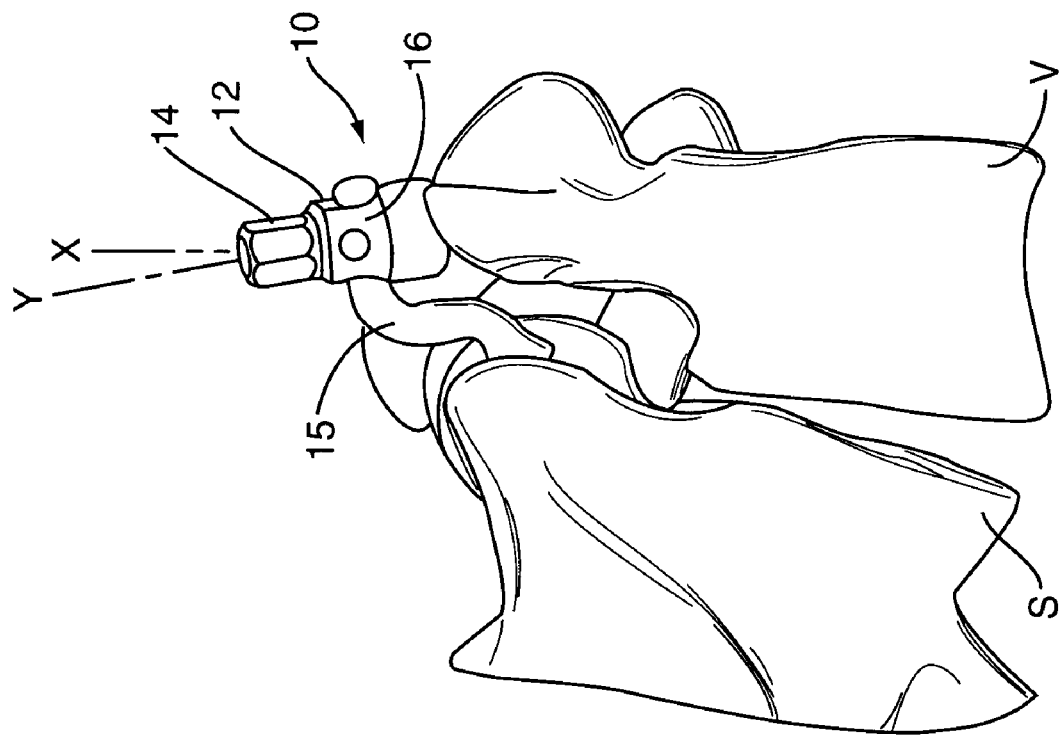
FIGS. 1A and 1B are perspective views of a pivoting head assembly according to one or more embodiments comprising a longitudinal member attached to the spine.
Figure 1B:
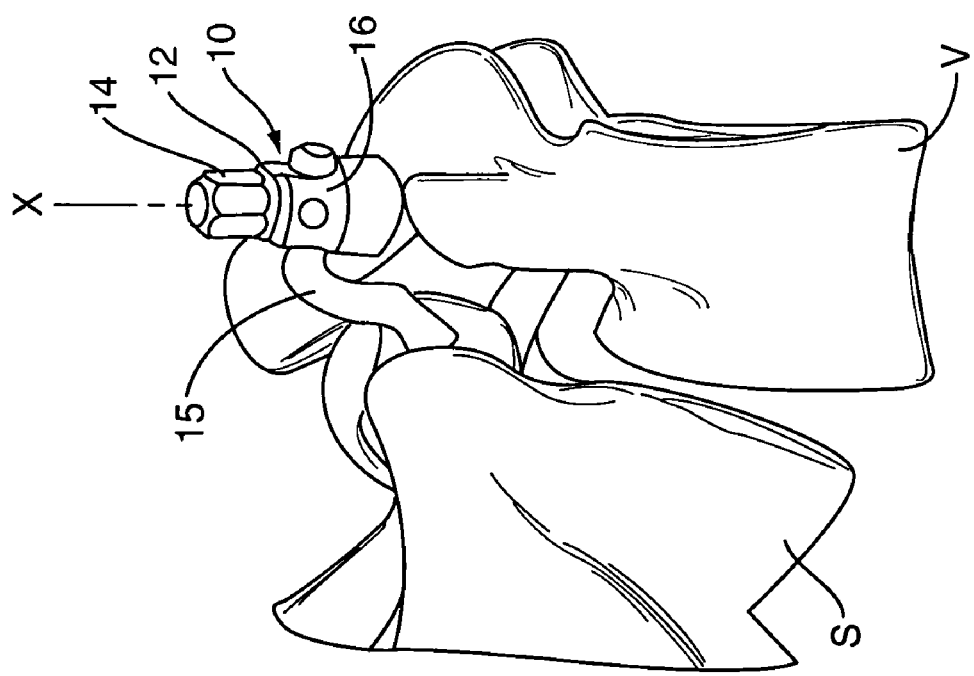

The various embodiments disclosed herein are directed to pivoting mechanisms and methods for securing longitudinal members in a spinal implant. Various types of longitudinal members are contemplated, including spinal rods that may be secured between multiple vertebral bodies. FIGS. 1A and 1B show another type of longitudinal member 15 that is secured between the sacrum S and a vertebral member V (i.e., L5). In one embodiment, the longitudinal member 15 is a flexible member, such as a resin or polymer compound. Some flexible non-metallic longitudinal members 15 are constructed from materials such as PEEK and UHMWPE. Other types of flexible longitudinal members 15 may comprise braided metallic structures. In one embodiment, the longitudinal member 15 is rigid or semi-rigid and may be constructed from metals, including for example stainless steels, cobalt-chrome, titanium, and shape memory alloys. Further, the longitudinal member 15 may be straight, curved, or comprise one or more curved portions along its length.

In FIGS. 1A and 1B, the longitudinal member 15 is secured to the vertebral member V with one embodiment of a pivoting head 10 in accordance with the teachings provided herein. In the embodiment shown, the longitudinal member 15 is secured to a saddle 16 within the pivoting head 10 with a securing member 12. The securing member 12 shown in FIGS. 1A and 1B features a snap-off driving member 14. The driving member 14 is integrally formed with the securing member 12 and allows a surgeon to drive the securing member 12 into contact with the longitudinal member 15 to achieve a certain installation torque. Above that torque, the driving member 14 will snap off, separating from the securing member 12. In this manner, the securing member 12 may provide the desired clamping force to secure the longitudinal member 15.

FIG. 1A shows a first orientation for the pivoting head 10 identified by the centerline labeled X. By contrast, FIG. 1B shows a second position representing a different spatial relationship between the sacrum S and the vertebra V. As compared to FIG. 1A, the vertebra V in FIG. 1B exhibits some amount of angular and torsional displacement relative to the sacrum S. Consequently, the pivoting head 10 is illustrated in a second orientation identified by the centerline labeled Y. The pivoting head 10 may provide some or all of this rotation. The illustrations provided in FIGS. 1A and 1B show the pivoting head 10 as part of a spinal implant that is coupled between a vertebral body V and a sacrum S. It should be understood that the pivoting head 10 may be used in constructs that are coupled to vertebral bodies V alone. Further, a vertebral implant may be construed to mean implants that are coupled to any or all portions of a spine, including the sacrum, vertebral bodies, and the skull.

Figure 2A:
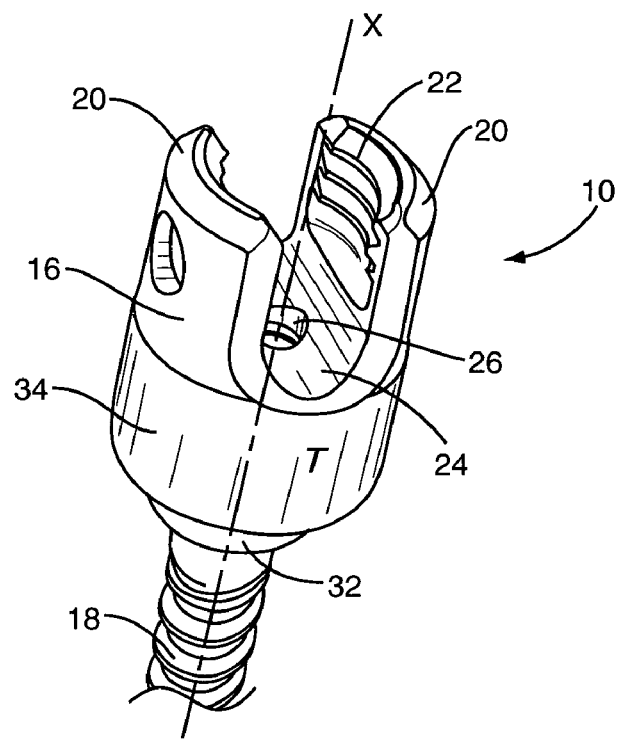
FIGS. 2A and 2B are perspective views of a pivoting head coupled to an anchor member according to one embodiment.
Figure 2B:
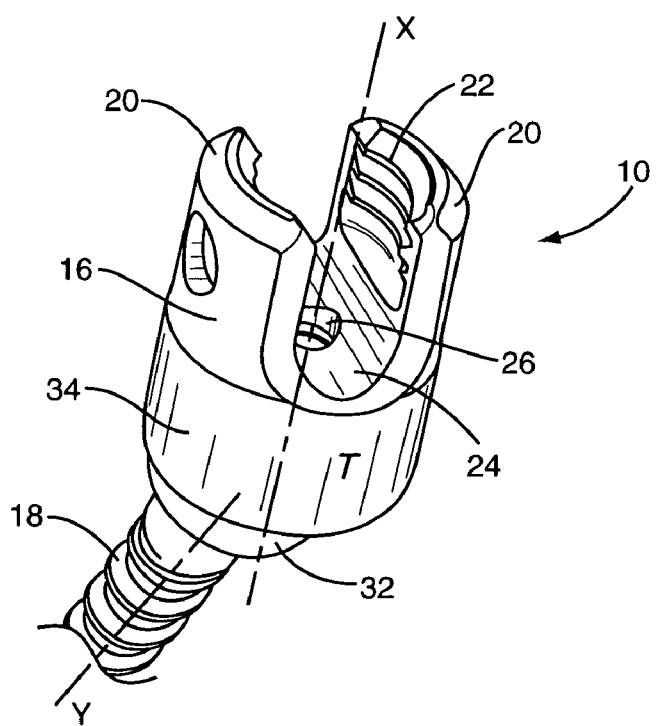

FIGS. 2A and 2B illustrate perspective views of the illustrative embodiment of the pivoting head 10 coupled to an anchor member 18. A head 32 of the anchor member 18 is pivotally coupled to a base portion 34 of the pivoting head 10. In one embodiment, the anchor member 18 comprises threads for insertion into a vertebral member V as shown in FIGS. 1A and 1B. In one embodiment, the anchor member 18 is a pedicle screw. The exemplary saddle 16 is comprised of opposed upright portions forming a U-shaped channel within which a longitudinal member 15 is placed. A seating surface 24 forms the bottom of the U-shaped channel. In one embodiment, the seating surface 24 is curved to substantially match the radius of a longitudinal member 15 that is positioned within the saddle 16. An aperture 26 within the seating surface provides access to a driving feature used to insert the anchor member 18 into a vertebral member V.

In FIG. 2A, the pivoting head 10 is shown substantially aligned with the anchor member 18 along the centerline labeled X. In FIG. 2B, the anchor member 18 is shown pivoted relative to the pivoting head 10. That is, the pivoting head 10 is shown still aligned with the centerline labeled X while the anchor member 18 is shown aligned with the centerline labeled Y. The pivoted displacement of the pivoting head 10 relative to the anchor member 18 achieved in FIG. 2B is provided by an articulation mechanism that is more clearly visible in the section view provided in FIG. 3.

Figure 3:
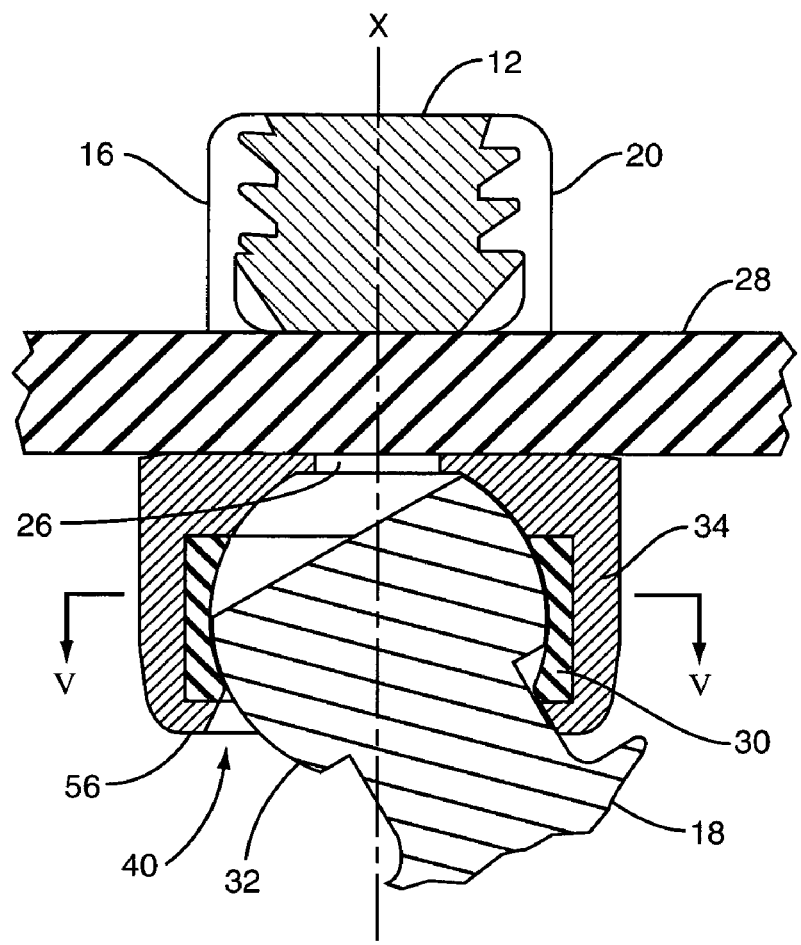
FIG. 3 is a side section view of a pivoting head coupled to an anchor member and securing a longitudinal member according to one embodiment.

FIG. 3 shows a section view of the pivoting head 10 holding a different type of longitudinal member 28. In this embodiment, the longitudinal member 28 is a spinal rod. The spinal rod 28 is secured within the saddle 16 with a securing member 12. In the embodiment shown, the securing member 12 is an externally threaded set screw, though other types of securing members such as externally threaded caps and nuts may be used. In the embodiment shown, an articulation mechanism 40 is disposed below the saddle 16 and generally aligned with the central axis X. The articulation mechanism 40 comprises an anchor head 32 of the anchor member 18 that is pivotally coupled to a wear member 30 within the base portion 34 of the pivoting head 10. Since the anchor head 32 is configured to pivot within the wear member 30, the wear member 30 and the outer surface of the anchor head 32 may be constructed of a wear resistance material. Some suitable examples may include hardened metals, titanium carbide, cobalt chrome, polymers, and ceramics.

In other embodiments, a wear resistant layer may be coated onto the anchor head 32 and the wear member 30. In one embodiment, the wear member 30 may be integrally formed into or form a part of the base portion 34. In one embodiment, the wear member 30 may be bonded to the base portion 34 using a biocompatible adhesive such as PMMA or other known adhesives. In these alternative embodiments, the part of the base portion 34 in contact with the anchor head 32 may be coated with a wear resistant layer. Coating processes that include, for example, vapor deposition, dip coating, diffusion bonding, and electron beam welding may be used to coat the above indicated materials onto a similar or dissimilar substrate. Diffusion bonding is a solid-state joining process capable of joining a wide range of metal and ceramic combinations. The process may be applied over a variety of durations, applied pressure, bonding temperature, and method of heat application. The bonding is typically formed in the solid phase and may be carried out in vacuum or a protective atmosphere, with heat being applied by radiant, induction, direct or indirect resistance heating. Electron beam welding is a fusion welding process in which a beam of high-velocity electrons is applied to the materials being joined. The workpieces melt as the kinetic energy of the electrons is transformed into heat upon impact. Pressure is not necessarily applied, though the welding is often done in a vacuum to prevent the dispersion of the electron beam.

The articulation mechanism 40 is spatially and functionally isolated from the clamping forces that are applied between the securing member 12, the rod 28, and the seating surface 24 (see FIGS. 2A, 2B). That is, since the compression forces applied by the securing member 12 are not transmitted to the articulation mechanism 40, the anchor member 18 rotates about the central axis X under the influence of the sliding resistance provided by the various embodiments disclosed herein. In this manner, the articulation mechanism 40 is not only spatially isolated from the securing member 12, but also physically isolated from the forces provided by the securing member 12.

Figure 4:
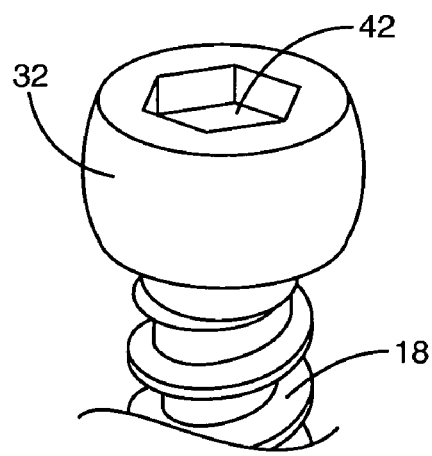
FIG. 4 is a perspective view of an anchor member for use with a pivoting head according to one embodiment.

FIG. 4 shows a perspective view of the anchor head 32 of the exemplary anchor member 18. The anchor head 32 includes a driving feature 42 that allows a surgeon to attach the anchor member 18 to a vertebra V. In the embodiment shown, a hex recess driving feature 42 is shown. Other types of driving features 42 may be appropriate, including for example, slotted, star, Torx, and cross-shaped features. The driving feature 42 may be accessed through the aperture 26 shown in FIGS. 2A, 2B, and 3.

Figure 5A:
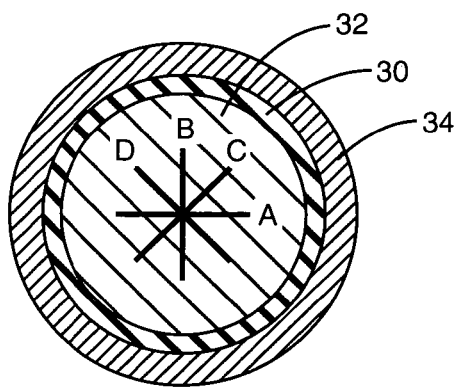
FIGS. 5A-5D are top section views of a pivoting head with an anchor member and wear member inserted therein according to different embodiments.
Figure 5B:
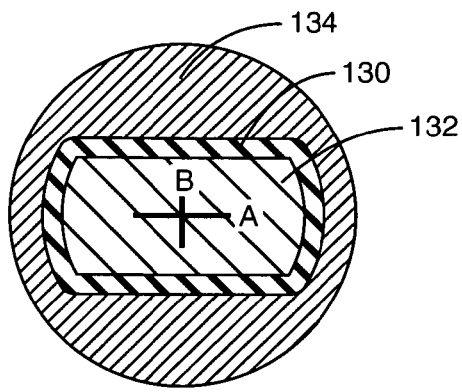
Figure 5C:
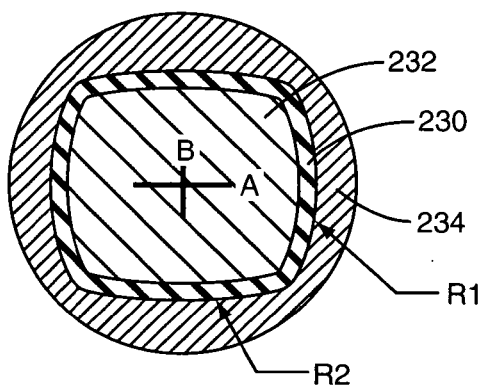
Figure 5D:
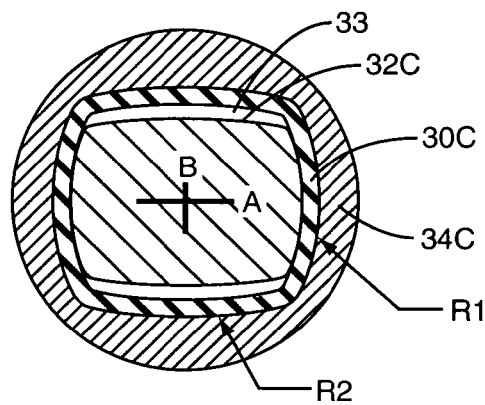

In the embodiment illustrated in FIG. 4, the anchor head 32 is substantially spherical to allow multi-axial pivoting of the anchor member 18 relative to the pivoting head 10. In other embodiments, the anchor head 32 has other shapes to allow motion in fewer directions. For instance, a disc-shaped anchor head 32 may provide motion within a desired plane. FIGS. 5A, 5B, and 5C illustrate some of these alternative embodiments. Specifically, FIGS. 5A-5D are top section views according to the section line V-V shown in FIG. 3. FIG. 5A shows one embodiment where the anchor head 32 and wear member 30 are substantially spherical as previously described. With this configuration, the pivoting head 10 may pivot about a plurality of axes, including axes A, B, C, and D as shown in FIG. 5A. The anchor head 32 may also rotate about an axis perpendicular to the page. FIG. 5B shows an alternative embodiment where the anchor head 32A and wear member 30A are substantially disc-shaped. As disclosed above, this configuration may allow pivoting motion about axis B, but not other axes, including axis A. FIG. 5C depicts another embodiment that is characterized by at least two different spherical radii R1, R2. This configuration may provide a different resistance to rotation of the anchor head 32B relative to wear member 30B about axes A and B. A somewhat pronounced difference in radii R1, R2 is shown in FIG. 5C, though in practice, a fairly small difference may produce the desired result. FIG. 5D depicts another embodiment similar to that shown in FIG. 5C, but with a limited amount of space 33 between the anchor head 32C and wear member 30C. Accordingly, the anchor head 32C may also rotate a limited amount relative to the wear member 30C about an axis perpendicular to the page. Note that the space 33 may be disposed between the anchor head 32C and wear member 30C as depicted, or between the wear member 30C and base portion 34C, or both to provide the limited rotation.

Figure 6A:
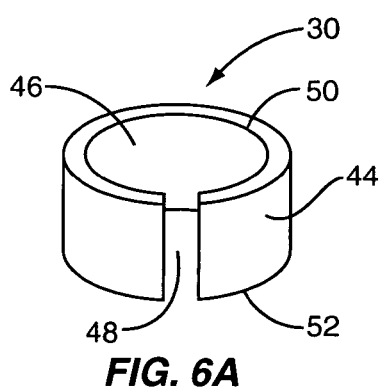
FIGS. 6A and 6B are perspective views of a wear member for use with a pivoting head according to one embodiment.

FIG. 6A shows a perspective view of a wear member 30 according to one embodiment. As depicted, the wear member 30 is cylindrically shaped and includes an outer surface 44 and an inner surface 46 extending between a top surface 50 and a bottom surface 52. Generally, the inner surface 46 is constructed to match the shape of the anchor head 32 of the threaded anchor member 18. The outer surface 44 may be configured as desired to fit within the base portion 34 of the pivoting head 10 as shown in FIG. 3. In one embodiment, the outer surface 44 is substantially cylindrical. The exemplary wear member 30 also includes a gap 48. The gap 48 in the present embodiment may be used to spread open the wear member 30 by an amount sufficient to slip the wear member 30 over the anchor head 32 of the anchor member 18.

Figure 6B:
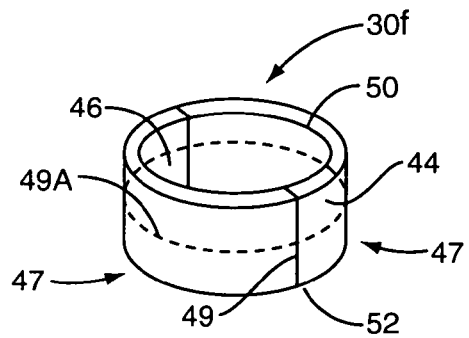
Figure 7:
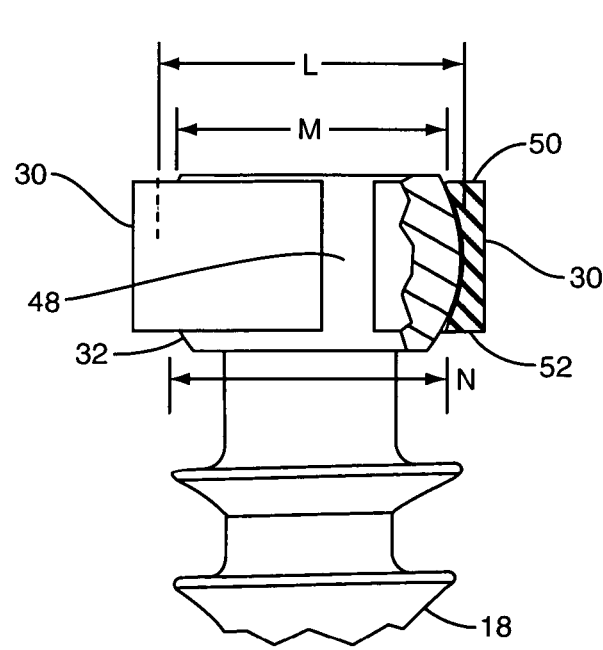
FIG. 7 is a side view, including a partial section view, of an assembled anchor member and wear member for use with a pivoting head according to one embodiment.

FIG. 6B shows a perspective view of a wear member 30f according to another embodiment. The wear member 30f is formed from separable halves 47 that may be joined at a parting line 49. Otherwise, the wear member 30f is shaped similar to the wear member 30 shown in FIG. 6A. That is, wear member 30f includes a generally cylindrical outer surface 44 and an inner surface 46 extending between a top surface 50 and a bottom surface 52. The halves 47 are separable and may be mirror images of each other, though this is not expressly required. Alternatively, or in addition, a parting line 49A depicted by dashed lines may extend parallel to the top surface 50 and bottom surface 52 to split the wear member 30f into quarters or into top and bottom halves. The wear member 30f may be split along different planes and into different numbers of pieces as desired or necessary. Essentially, the split wear member 30f may be separated to assemble the wear member 30f over the anchor head 32 of the anchor member 18 prior to insertion of the wear member 30f and anchor member 18 into the pivoting head 10. By eliminating the need to flex the wear member 30f during assembly, the separable wear member 30f may be constructed of substantially rigid, wear resistant materials, including for example ceramics, metal alloys, or relatively inelastic composites. The separable wear member 30f may be constructed of elastic materials as well. Further, The wear member 30 is shown installed on the anchor head 32 in FIG. 7. FIG. 7 also shows relevant dimensions of the wear member 30 and the anchor head 32. Dimension L represents a width of the anchor head 32 at its widest point. The width may comprise a diameter, a spherical diameter, or other linear dimension. Dimensions M and N respectively represent an interior width at the top 50 and bottom 52 of the wear member 30. Notably, dimension L is larger than both M and N. Thus, the gap 48 allows the anchor head 32 to fit within the wear member 30 as shown in FIG. 7.

Figure 8:
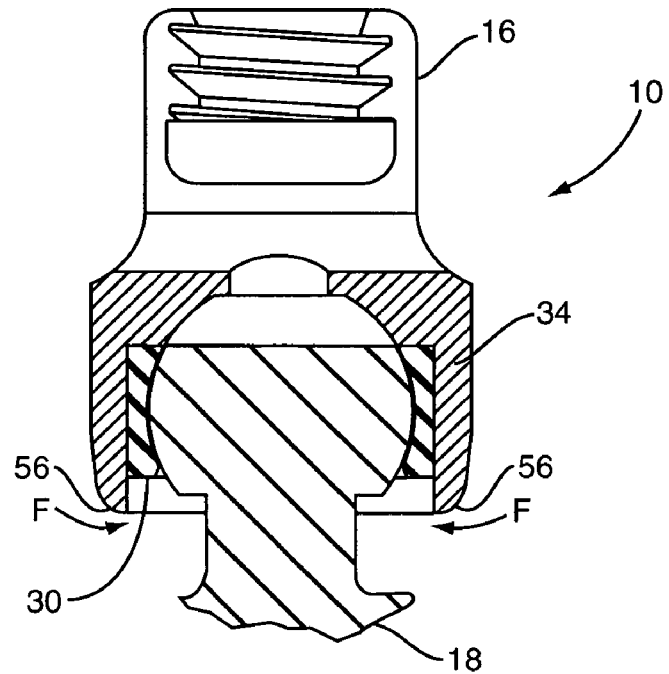
FIG. 8 is a side section view of a pivoting head with an anchor member and wear member inserted therein according to one embodiment.
Figure 9:
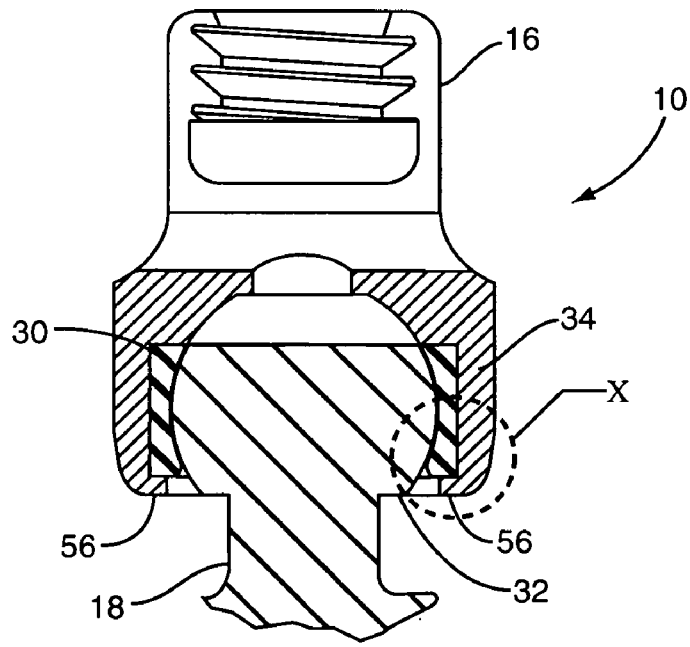
FIG. 9 is a side section view of an assembled pivoting head with an anchor member and wear member constrained therein according to one embodiment.

FIG. 8 shows the assembled wear member 30 and anchor member 18 inserted into the base portion 34 of the pivoting head 10. The anchor member 18 and wear member 30 are retained within the base portion 34 by deforming the lower lip 56 in the direction of the arrow labeled F. The deforming step may be performed using a variety of techniques, including but not limited to mechanical pressing, swaging, and orbital forming. Orbital forming (or orbital forging) is a cold metal forming process during which the workpiece (the base portion 34 in this case) is transformed between upper and lower dies. The process features one or the other of these dies orbiting relative to the other with a compression force applied therebetween. Due to this orbiting motion over the workpiece, the resultant localized forces can achieve a high degree of deformation at a relatively low compression force level. The fully assembled pivoting head 10 is illustrated in FIG. 9. In this Figure, the lower lip 56 of the base portion 34 is formed to constrain the wear member 30 and the anchor member 18.

Figure 10:
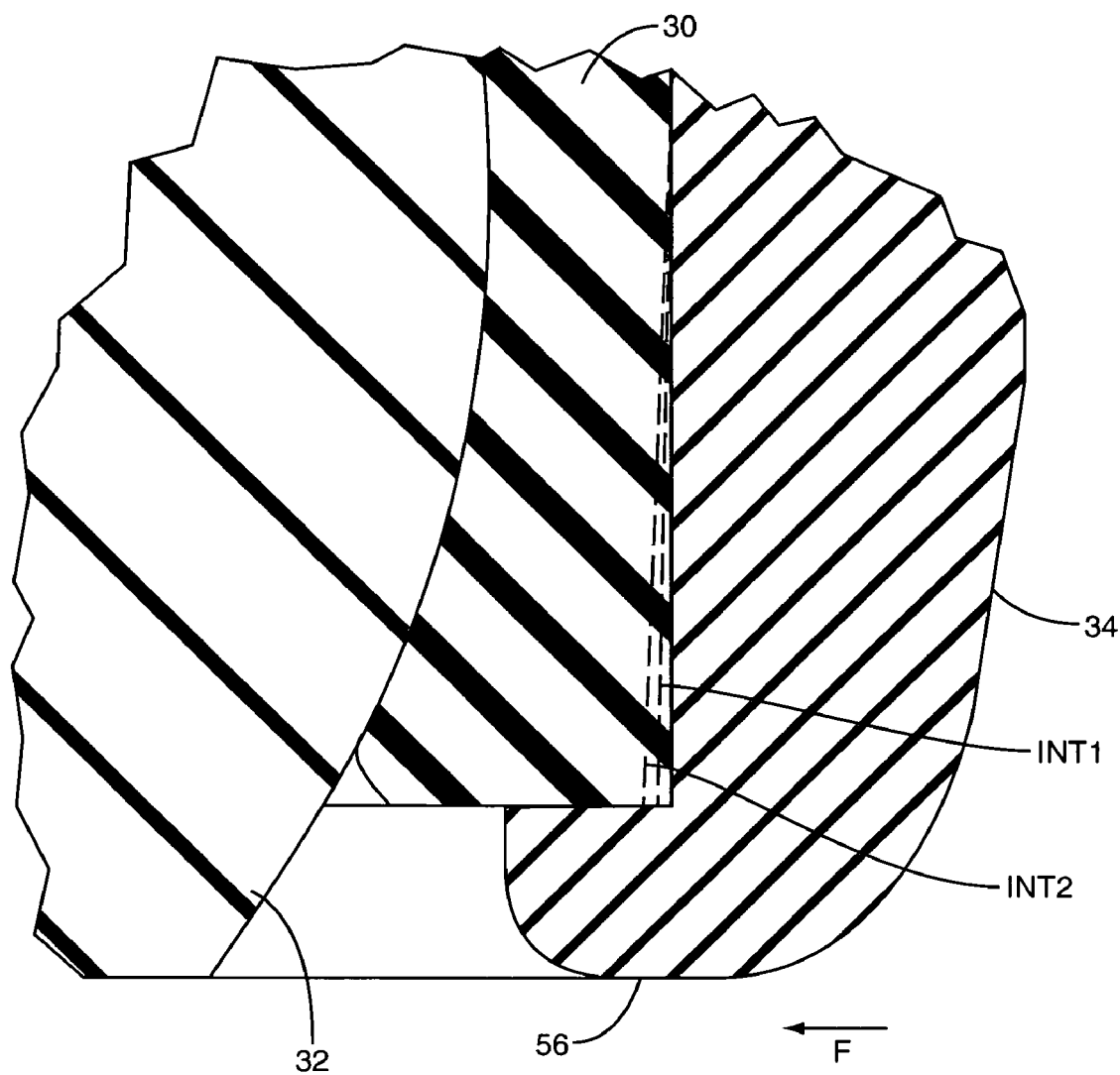
FIG. 10 is a detailed section view of the bottom region of a pivoting head according to one embodiment.

FIG. 10 shows a detail view of the lower lip 56 of the base portion 34. The forming technique used to form the lower lip 56 under and around the wear member 30 may be controlled to produce a pivoting head 10 with a desired, predetermined resistance to motion. The dashed lines labeled INT1 and INT2 depict this ability to control the amount of interference between the parts, and hence the amount of resistance to motion. If a greater amount of resistance to motion is desired, the lower lip 56 may be deformed a greater amount as indicated by the dashed line labeled INT2. A lesser amount of deformation indicated by the dashed line INT1 may produce less resistance to motion. In one embodiment, the lower lip 56 is formed to produce a very large resistance to motion such that the pivoting head 10 is, for all practical purposes, fixed. At the opposite end of the spectrum, the lower lip 56 is formed to merely place the relevant parts (base portion 34, wear member 30, and anchor head 32) in contact with one another or in close proximity to one another. In this embodiment, the pivoting head 10 is free to rotate with very little or no resistance to motion. At points between these extremes (indicated by dashed line INT1), a desired amount of interference may produce a desirable resistance to motion.

The resistance to motion may be measured in standard torque units, such as inch-ounces or other units of measure. As the parts are formed, the measurable resistance to motion may be marked on the exterior of the pivoting head 10 to provide surgeons an indication of the relative flexibility of the pivoting head 10. This marking may be provided as an alphanumeric indication as represented by the letter T in FIGS. 2A and 2B. The marking may be stamped, whether by ink or metal deformation, engraved, or otherwise displayed on the pivoting head 10.

Figure 11:
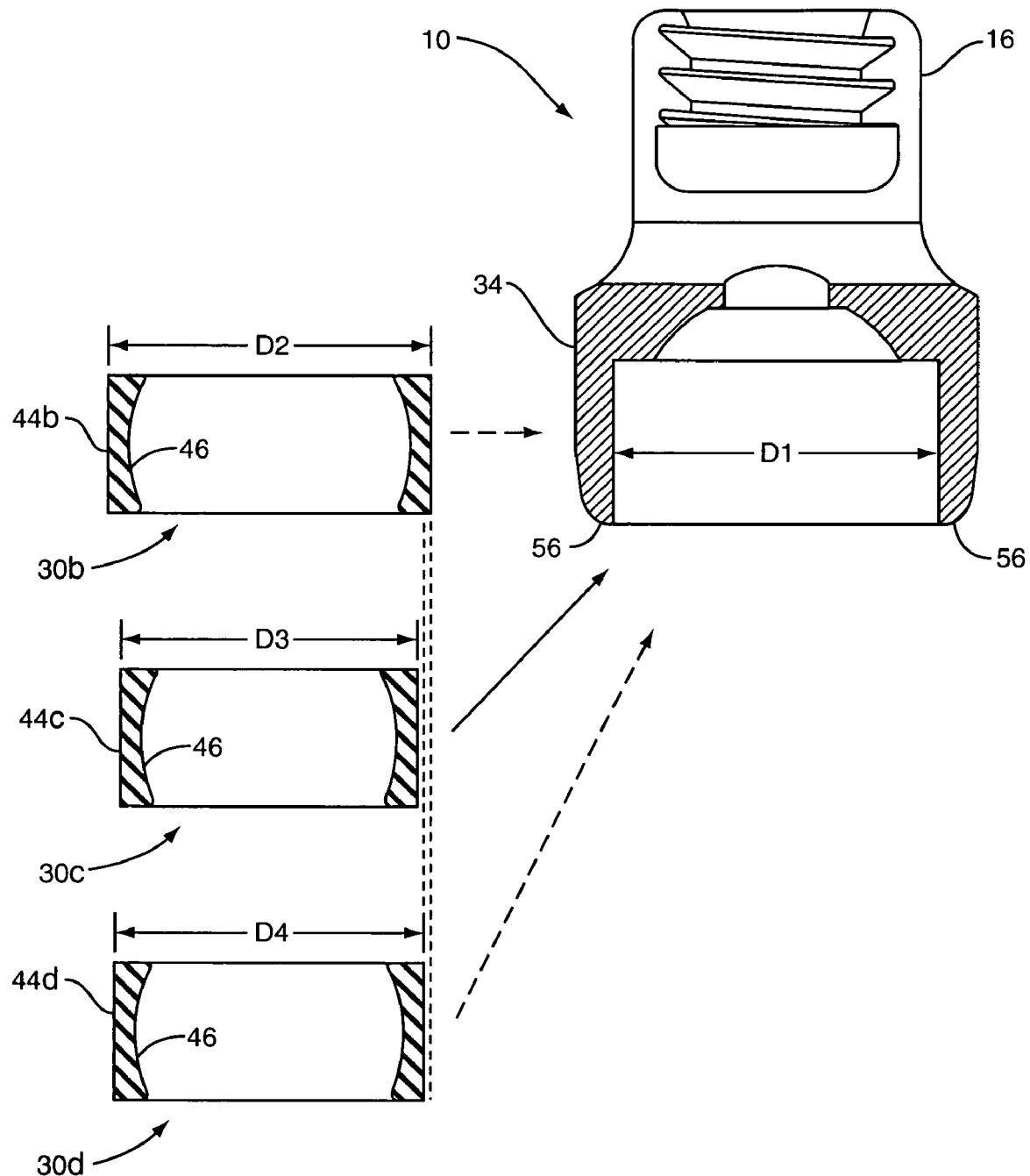
FIG. 11 is a side section view of a pivoting head and various wear members that may be used with the pivoting head according to one embodiment.

Interference between the base portion 34, the wear member 30, and the anchor head 32 will generally contribute to greater amounts of resistance to motion. Accordingly, the parts may be selected according to size to provide the desired resistance to motion. For instance, FIG. 11 shows a pivoting head 10, including a base portion 34 that is defined in part by a dimension D1. This dimension D1 corresponds approximately to the outer dimension of the wear members 30b, 30c, and 30d that are also shown in FIG. 10. However, each wear member 30b-d has a slightly different outer dimension D2-D4. As an example, wear member 30b is characterized by the largest outer dimension D2. Wear member 30c is characterized by the smallest outer diameter D3 and wear member 30d is somewhere between, with an outer diameter D4. It is assumed for the sake of this discussion, that the inner surface 46 is the same for all three wear members 30b-d. In an alternative embodiment, the inner surface 46 may be constructed with different sizes to create different amounts of interference with the anchor head 32 of the anchor member 18. In an alternative embodiment, both the inner 46 and outer 44 surfaces may vary between wear members 30. That is, different wear members 30 may have different thicknesses. In an alternative embodiment, the resistance to pivoting motion of the head 32 may be provided by materials having different coefficients of friction.

For the embodiments shown in FIG. 11, wear member 30c will result in the least amount of interference when used in the pivoting head 10. Conversely, wear member 30b will result in the greatest amount of interference when used in the pivoting head 10. A measurable resistance to motion of the pivoting head 10 can be determined once the parts are assembled. As indicated above, this measured resistance to motion may be marked on the exterior of the pivoting head 10 to provide surgeons an indication of the relative flexibility of the pivoting head 10.

Figure 12:
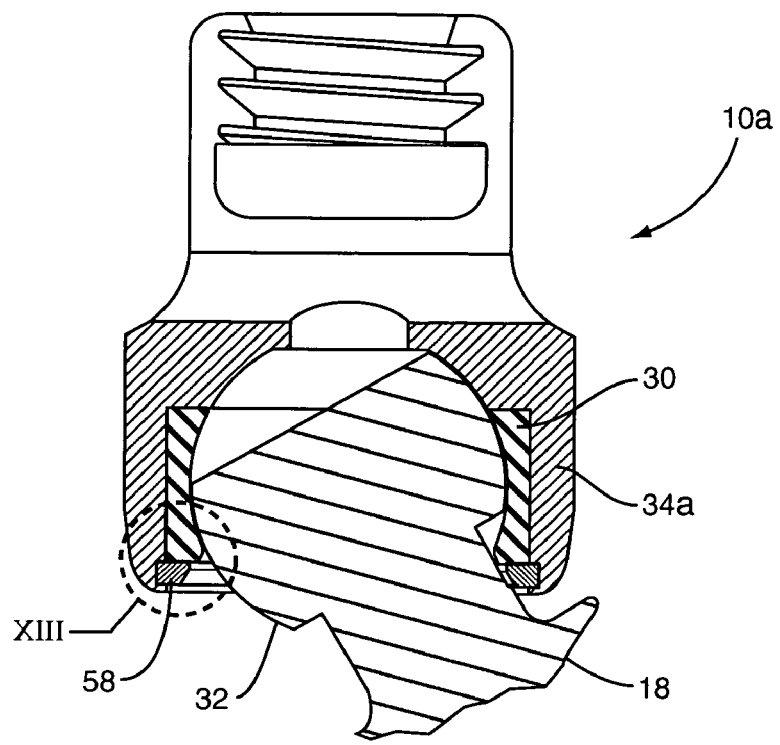
FIG. 12 is a side section view of an assembled pivoting head with an anchor member and wear member constrained therein according to one embodiment.
Figure 13:
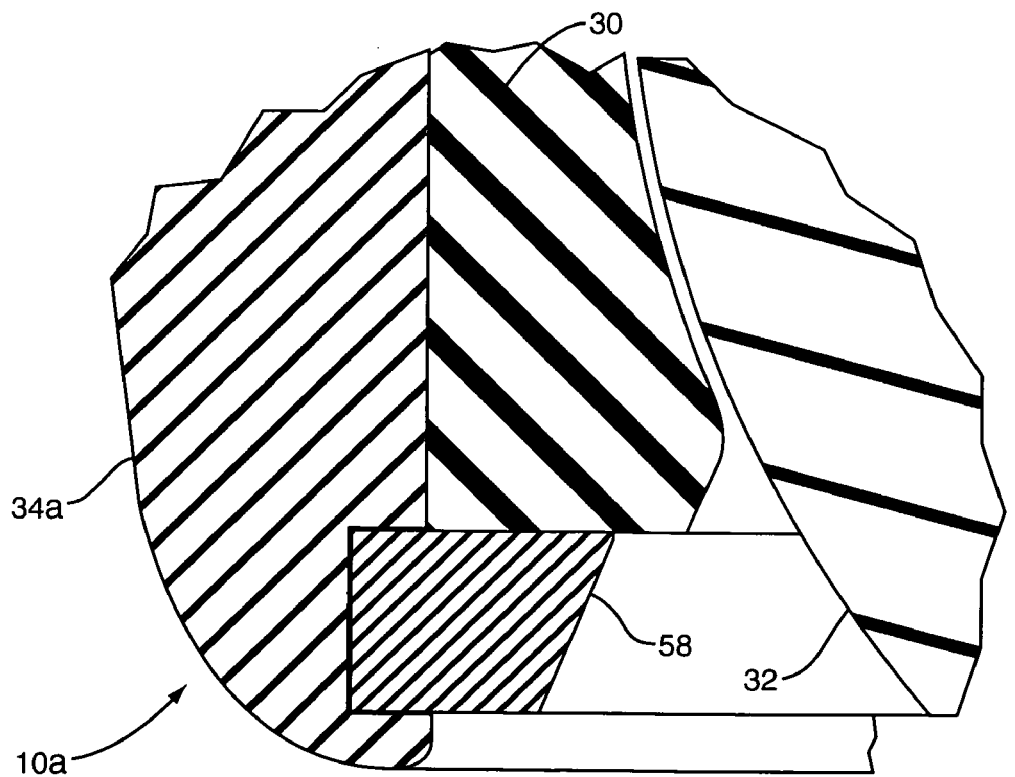
FIG. 13 is a detailed section view of the bottom region of a pivoting head according to one embodiment.

FIG. 12 shows an alternative embodiment of the pivoting head 10a. The section view shows an alternative technique for retaining the wear member 30 and anchor member 18 within the base portion 34a. In this embodiment, a snap ring 58 is inserted into the bottom of the base portion 34a beneath the wear member 30. The snap ring 58 may effectively retain the wear member 30 and anchor member 18 within the pivoting head 10a. A detailed view of the area around the snap ring 58 is shown in FIG. 13. Notably, in this embodiment, the snap ring 58 acts as a barrier to prevent the wear member 30 from escaping but does not contribute to any interference between the other parts (30, 32, 34).

Figure 14:
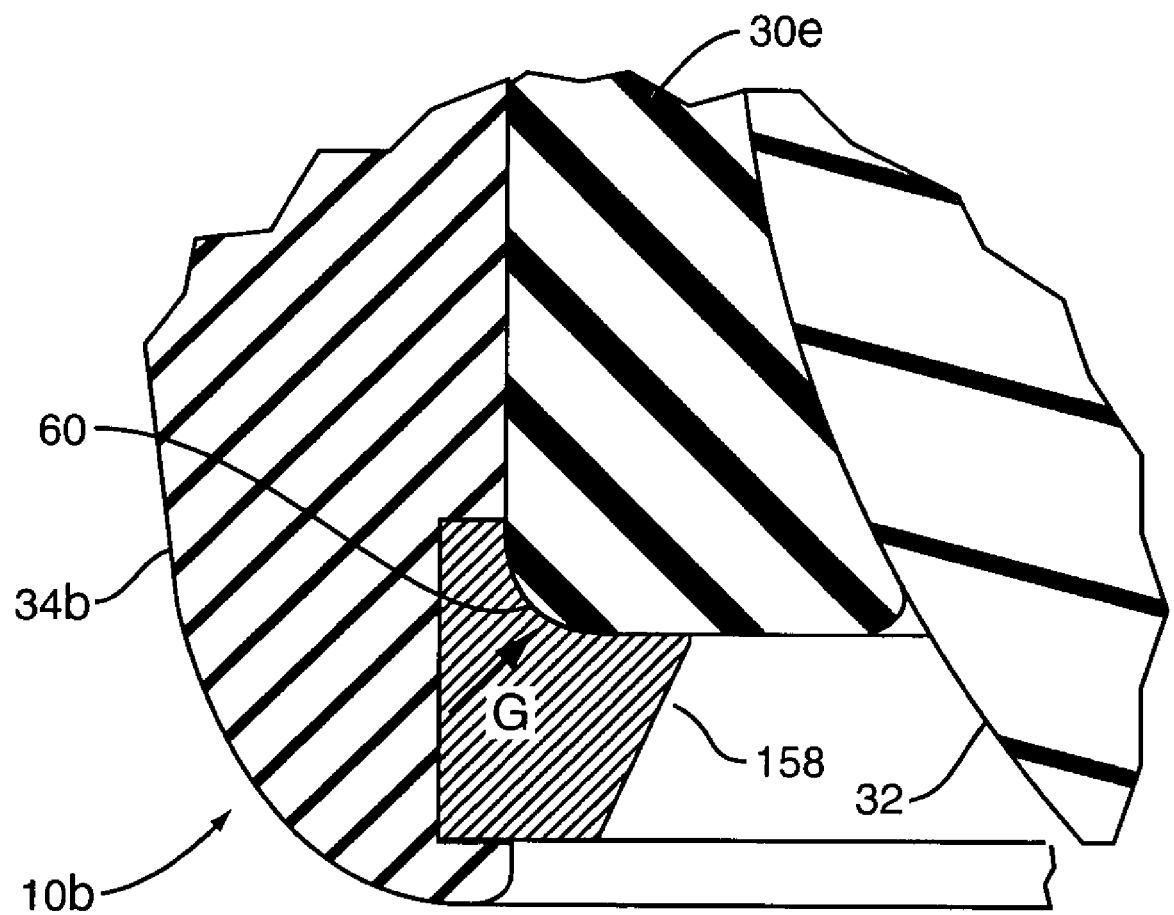
FIG. 14 is a detailed section view of the bottom region of a pivoting head according to one embodiment.

In an alternative embodiment shown in FIG. 14, a snap ring 158 may contribute to the overall resistance to motion of the pivoting head 10b. As with the embodiment shown in FIGS. 12 and 13, the snap ring 158 is configured to fit within the interior of the base portion 34b. However, the interior portion of the snap ring 158 is modified slightly to create an interference with the wear member 30e. In this embodiment, the wear member 30e is slightly modified to include a rounded lower outside corner 60 to facilitate insertion of the snap ring 158. A detailed view of a cross section of the snap ring 158 is shown in FIG. 15.

The exemplary snap ring 158 comprises a bottom surface 64, a top surface 66, and an outer surface 62, each of which are configured to fit within the body portion 34b of the pivoting head 10b. A retaining surface 68 further acts to keep the wear member 30e within the pivoting head 10b. This snap ring 158 also includes an interference surface 70 that contacts the wear member 30e to create a force G (shown in FIG. 14) that compresses the wear member 158 towards the anchor head 32. The compression force G creates an interference that resists pivoting motion of the anchor head 32 relative to the wear member 30e. Snap rings 158 including different interference surfaces 72, 74 may be selected to create more or less interference as desired. Once the snap ring 158 is assembled to retain and compress the wear member 30e, a measurable resistance to motion of the pivoting head 10b can be determined. As indicated above, this measured resistance to motion may be marked on the exterior of the pivoting head 10b to provide surgeons an indication of the relative flexibility of the pivoting head 10b.

Figure 16:
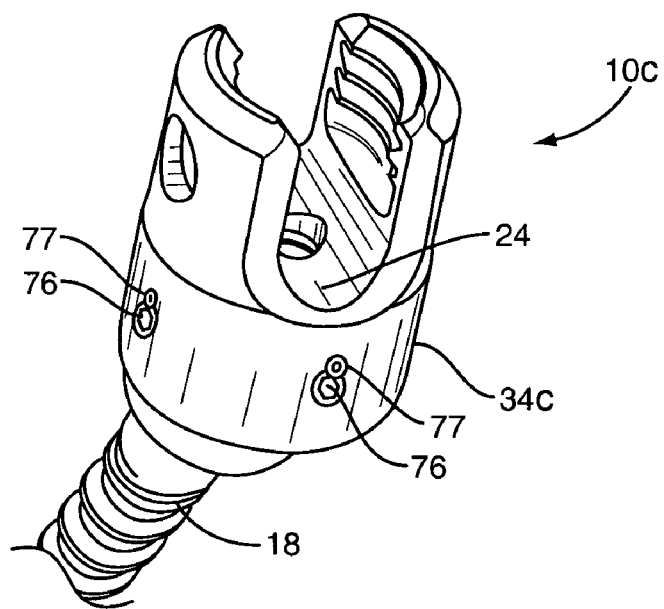
FIG. 16 is a perspective view of a pivoting head coupled to an anchor member according to one embodiment.
Figure 17:
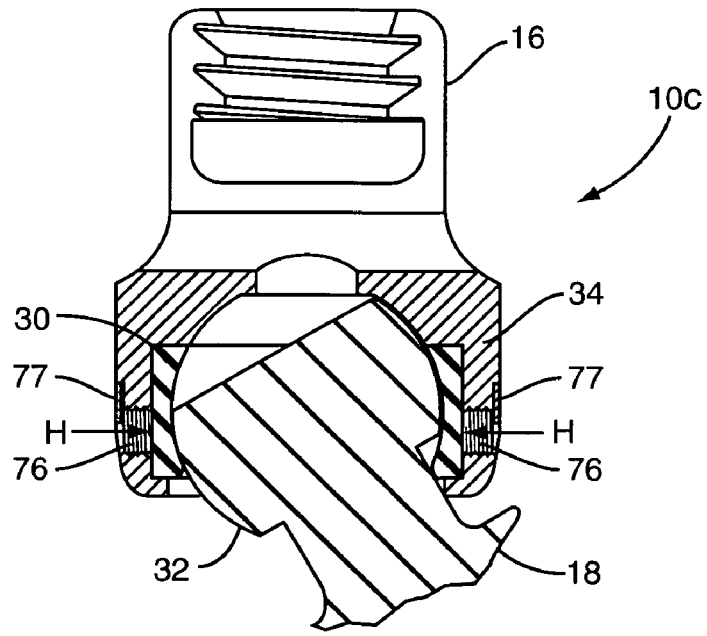
FIG. 17 is a side section view of an assembled pivoting head with an anchor member and wear member constrained therein according to one embodiment.

FIGS. 16 and 17 illustrate an alternative embodiment of the pivoting head 10c. In this embodiment, the resistance to motion may be set intra-operatively. The base portion 34C of the pivoting head 10c includes one or more adjustment members 76 that allow a surgeon to adjust the amount of interference between the wear member 30 and the anchor head 32. Further, a surgeon may be able to adjust this amount of interference differently about different axes depending upon how many adjustment members 76 are provided. In the embodiments illustrated, there are four total adjustment members 76, disposed approximately 90 degrees apart from one another. More or fewer adjustment members 76 may be provided. Also, in one embodiment, one of the adjustment members 76 is substantially aligned with the orientation in which a longitudinal member 15 lies. For example, in the embodiment shown, one adjustment member 76 is substantially parallel to the seating surface 24. In one embodiment, an adjustment member 76 is substantially transverse to this seating surface. In the embodiment shown, the adjustment members 76 are setscrews that may be screwed in to create a compressive force H that is shown in FIG. 17. In another embodiment, the adjustment member 76 may be a pin. The compressive force H may create an increased amount of interference that also creates more resistance to motion.

In one embodiment, the adjustment member 76 may be retained using a locking member 77. The locking member 77 may be sized and positioned to prevent the adjustment member 76 from backing out of the base portion 34C. In one embodiment, the locking member 77 may be sized and positioned to maintain a desired compression by the adjustment member 76. The locking member 77 may be similar to locking mechanisms used in the Zephir™ cervical plates available from Medtronic, Spinal & Biologics Division in Memphis, Tenn., USA. Other examples of locking members 77 suitable for use in the present embodiment are disclosed in commonly assigned U.S. patent application Ser. No. 10/870,026 filed Jun. 17, 2004 and U.S. patent application Ser. No. 11/150,506 filed Jun. 10, 2005, the contents of each being incorporated by reference herein in their entirety.

Figure 18:
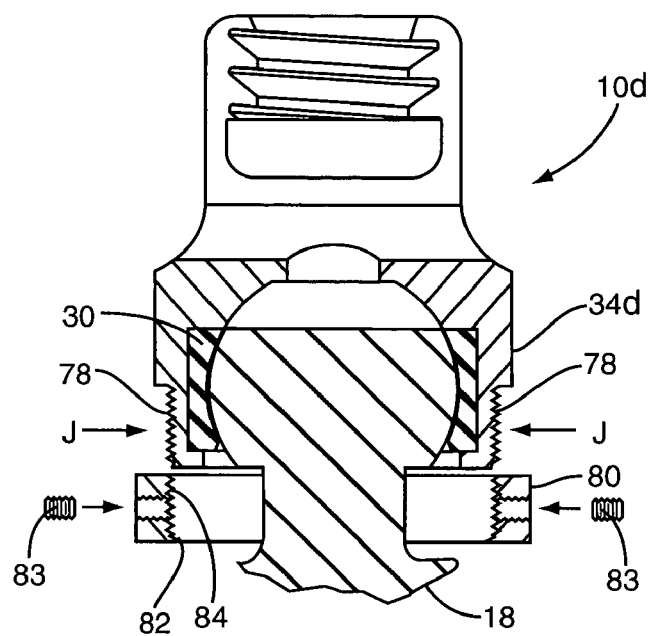
FIG. 18 is a side section view of an assembled pivoting head with an anchor member and wear member constrained therein according to one embodiment.

FIG. 18 shows an alternative embodiment of the pivoting head 10d that includes a threaded region 78 disposed towards a bottom of the base portion 34d. An adjustment member 80 having substantially matching threads 84 is threaded onto the threads 78 on the base portion 34d and rotated until the desired resistance to motion is obtained. This procedure may be performed intra-operatively. In one embodiment, the threads 78, 84 are tapered threads to create an increasing amount of inward compression J and corresponding interference. In one embodiment, a lower opening 82 of the adjustment member 80 is smaller than a width of the threaded portion 78 of the base portion 34d. Consequently, the more the adjustment member 80 is threaded onto the base portion 34d, the base portion 34d is compressed an increasing amount.

In one embodiment, the adjustment member 80 may be retained using a locking member 83. The locking member 83 may be implemented as a setscrew as illustrated, though other members (e.g., pins, clips), features, or process steps may be used. For example, the adjustment member 80 may be staked in a desired position once the desired amount of compression is achieved. The locking member 83 may be sized and positioned to prevent the adjustment member 76 from backing out from the base portion 34d. In one embodiment, the locking member 83 may be sized and positioned to maintain a desired compression by the adjustment member 80.

Figure 19:
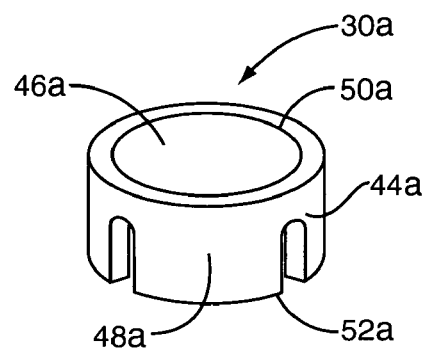
FIG. 19 is a perspective view of a wear member for use with a pivoting head according to one embodiment.

FIG. 19 shows an alternative embodiment of the wear member 30a that may be used in one or more embodiments disclosed herein. The wear member 30a also includes a series of gaps 48a as with the previous embodiment shown in FIG. 6. However, gaps 48a do not extend from the bottom surface 52a to the top surface 50a. In this embodiment, the top surface 50a of the wear member 30a is substantially continuous. In one embodiment, the wear member 30a comprises four gaps 48a separated by approximately 90 degrees. In other embodiments, more or fewer numbers of gaps 48a are used. Since the gaps 48a originate at the bottom surface 52a of the wear member 30a, inward deflection of the wear member 30a, particularly near the bottom surface 52a, is possible. This feature may be appropriate for one or more embodiments where inward deflection of the wear member 30a is used to create a desired resistance to motion.

Figures 20, 21:
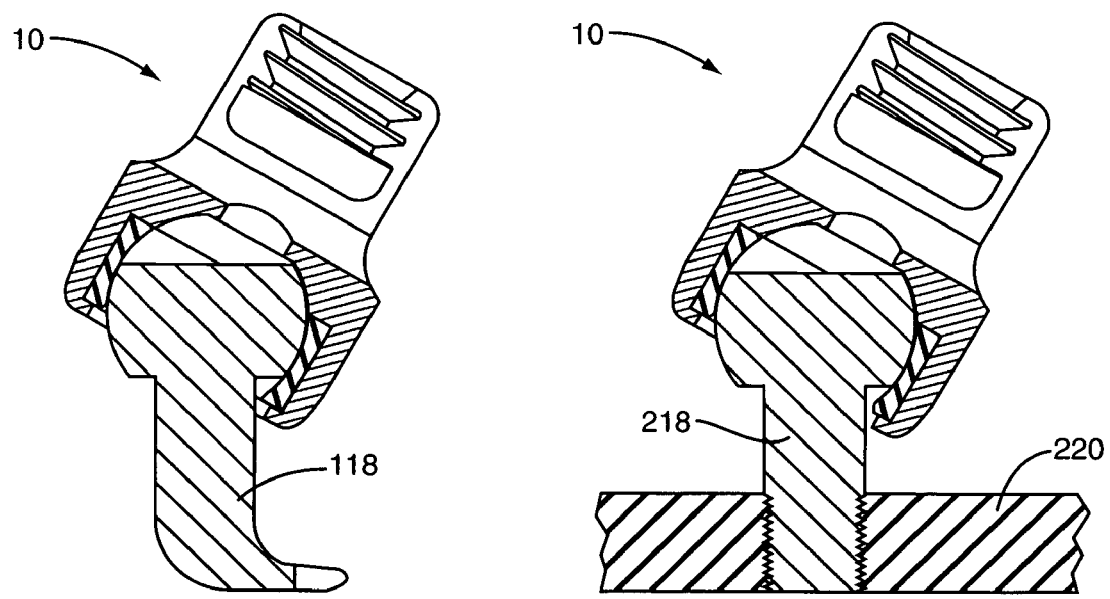
FIG. 20 is a side section view of an assembled pivoting head with an anchor member and wear member constrained therein according to one embodiment.
FIG. 21 is a side section view of an assembled pivoting head with an anchor member and wear member constrained therein according to one embodiment.
Figure 23:
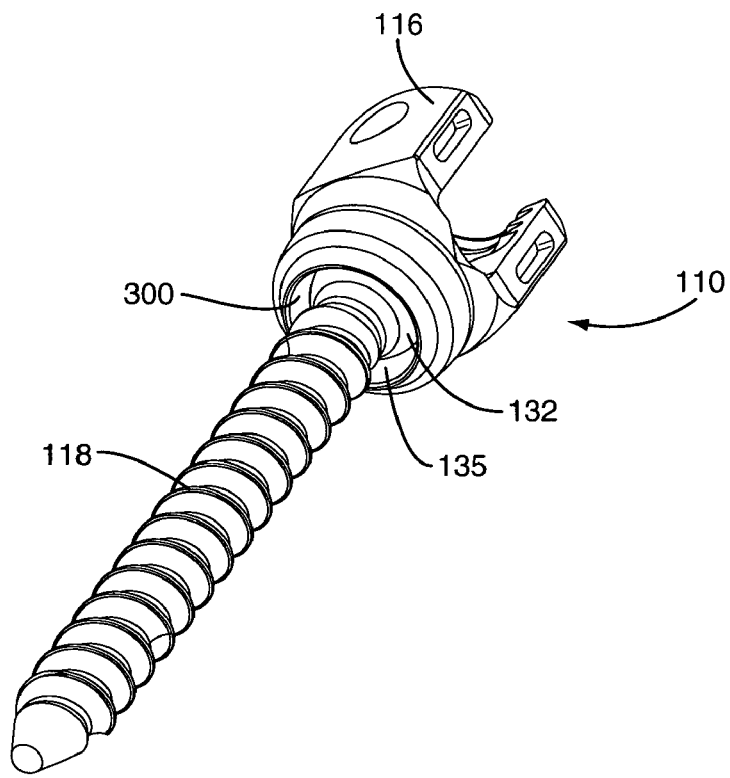
FIG. 23 is a lower perspective view of a pivoting head coupled to an anchor member according to one embodiment.

Embodiments described above have contemplated an anchor member 18 that comprises threads for insertion into a vertebral member V. Certainly, the pivoting head 10 may be incorporated on other types of bone screws. For example, different types of screws may be used to attach longitudinal members 15 to the sacrum S or to other parts of a vertebral member V. These include, for example, anterior and lateral portions of a vertebral body. In other embodiments, such as those shown in FIGS. 20 and 21, the pivoting head 10 may be implemented on other types of anchoring members. For example, FIG. 20 shows a pivoting head 10 incorporated onto a hook-type anchor member 118. In another embodiment shown in FIG. 21, the pivoting head 10 is incorporated onto another type of threaded anchor member 218 that is inserted into a plate 220 instead of a bony member.

Embodiments of the pivoting head 10 described above incorporate a controlled resistance to motion that is isolated, both spatially and functionally, from the clamping forces that are applied between the securing member 12, the rod 28, and the rod seating surface 24. The clamping forces are isolated from the enlarged screw head 32. In contrast with these aforementioned embodiments, FIGS. 22-25 depict embodiments with a pivoting head 110 that is configured to accept a crown 300 that is shaped and positioned to transmit clamping forces that are applied between the securing member 12 and the rod 28 onto the head 132 of the anchor member 118. With this configuration, the crown 300 secures or controls the motion of the anchor member 118 through the application of a clamping force provided by the securing member 12.

In the illustrated embodiment, the pivoting head 110 is similar to previously described embodiments in that it includes an upper saddle 116, a rod seating surface 124, and a base portion 134. The base portion 134 includes an opening 126 opposite the upper saddle 116. The opening 126 includes a substantially uniform width up to a stop surface 129. The opening 126 and the stop surface 129 at least partially intersect the seating surface 124. Further, the opening 126 is sized to accept the crown 300.

The crown 300 is generally cylindrical and includes a top surface 131, a bottom surface 137 and a perimeter surface 139 extending substantially therebetween. An access hole 141 is formed in the top surface 131 and provides access to a driving feature 142 in the head 132 of the anchor member 118. Thus, when the separate pieces are assembled as shown in FIGS. 22B-25, the driving feature 142 is accessible through the access hole 141.

A contoured bearing surface 135 forms a socket into which the enlarged head 132 of the anchor member 118 is inserted. In one embodiment, the bearing surface 135 is substantially spherical. In one embodiment, the bearing surface 135 includes a spherical size that is substantially similar to that of the head 132.

Figure 25:
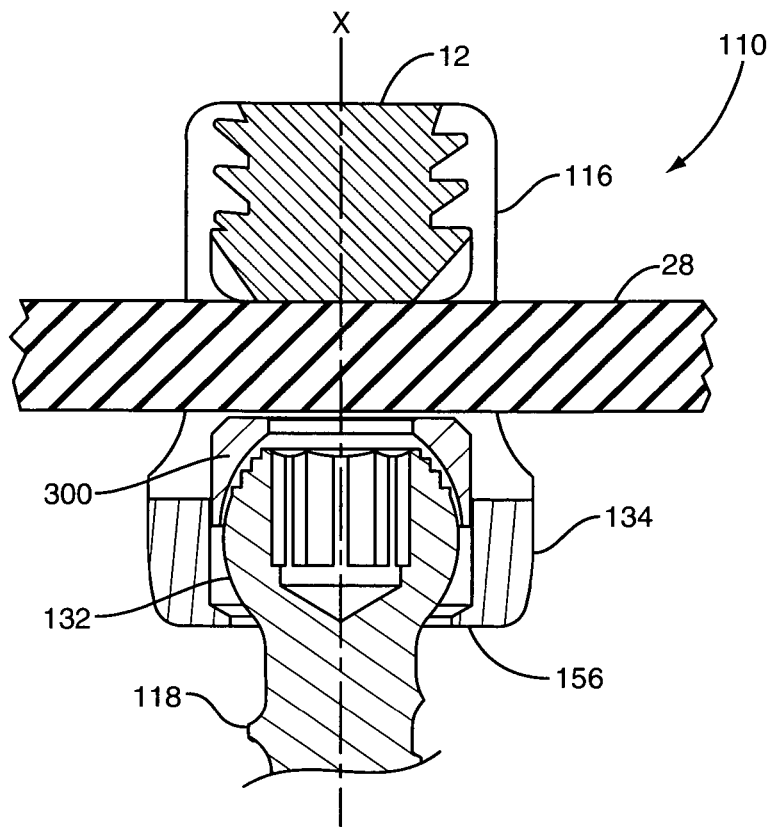
FIG. 25 is a side section view of a pivoting head with a crown member and anchor head retained therein according to one embodiment.

In the illustrated embodiment, the head 132 of the anchor member 118 includes a plurality of serrations 133 that configured to engage the bearing surface 135 once a sufficient clamping force is applied onto the rod 28 and onto the crown 300, by the securing member 12 (see FIG. 25). The serrations 133 or other friction enhancing features may be used to secure the position of the anchor member 118 once the securing member 12 is tightened within the upper saddle 116 and onto the rod 28. However, in other embodiments, the enlarged head 132 may be polished or smooth such that the head 132 may articulate and slide relative to the bearing surface 135 even after the securing member 12 is tightened within the upper saddle 116.

The anchor member 118 and crown 300 are retained within the base portion 134 by deforming the lower lip 156 in the direction of the arrow labeled F. As disclosed above, the deforming step may be performed using a variety of techniques, including but not limited to mechanical pressing, swaging, hot forming, cold forming, and orbital forming. FIG. 25 shows an enlarged view of the pivoting head 110 with the lower lip 156 deformed to retain the anchor member 118 and crown 300.

Figure 24:
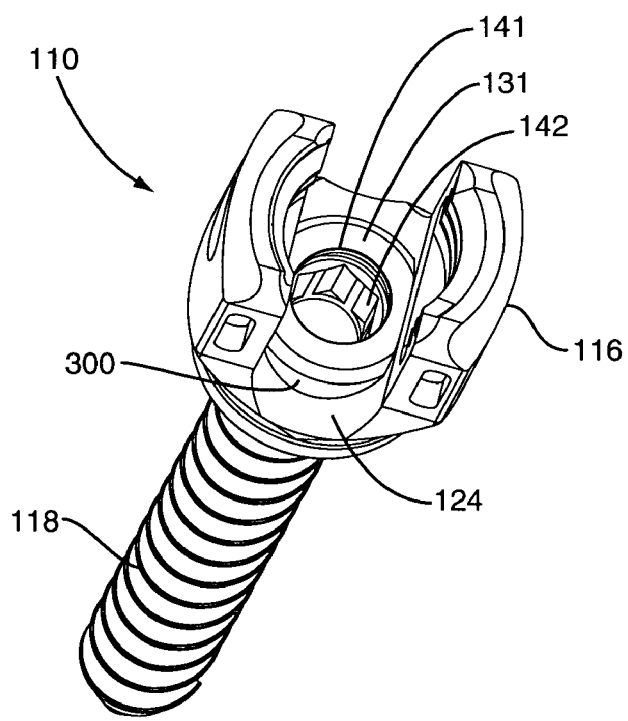
FIG. 24 is an upper perspective view of a pivoting head coupled to an anchor member according to one embodiment.

FIGS. 22B, 24, and 25 show the crown 300 inserted into the pivoting head 110 with the insertion depth limited by the stop surface 129. Once inserted, the top surface 131 of the crown 300 lies above the rod seating surface 124. Therefore, once a rod 28 (FIG. 25) is inserted into the upper saddle 116, the rod 28 contacts the top surface 131. Consequently, a securing member 12 (FIG. 25) imparts a clamping force onto the rod 28, which in turn, compresses the crown 300 between the rod 28 and the anchor head 132 to secure or limit the pivoting movement of the anchor member 118.

Figures 26A, 26B:
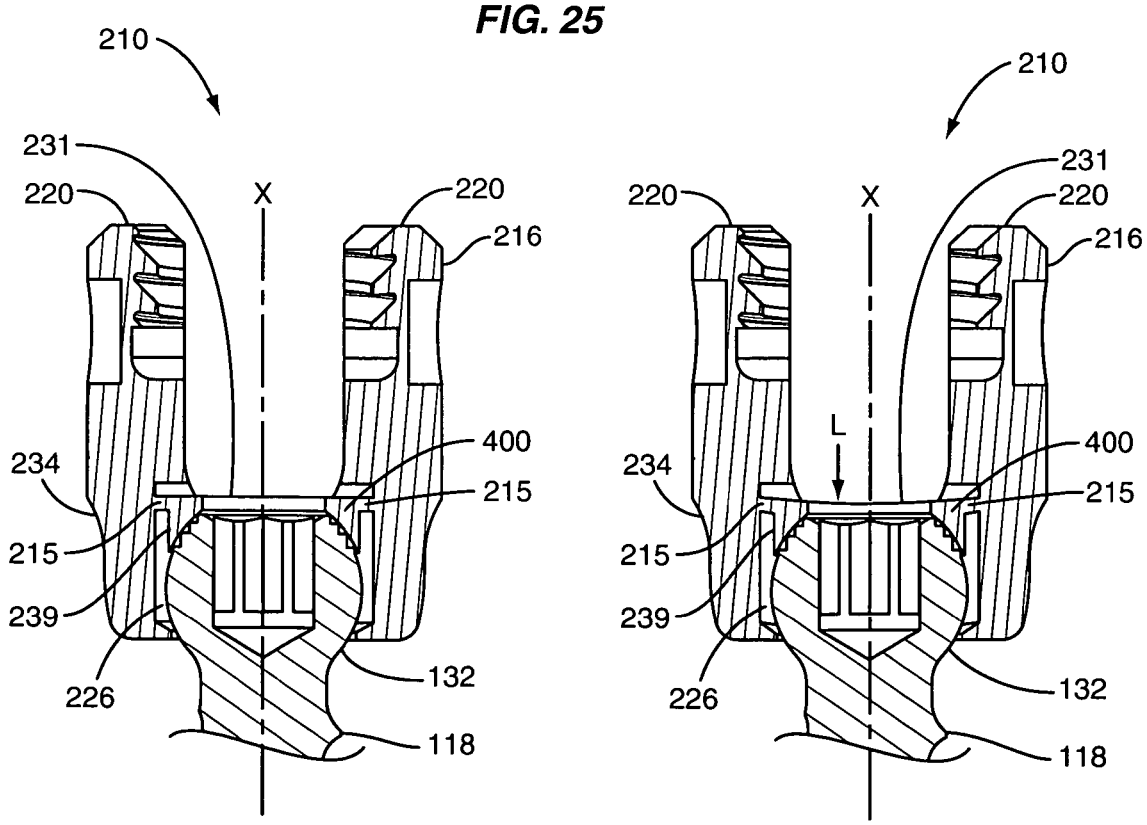
FIGS. 26A and 26B are side section views of a pivoting head with a deflectable crown member and anchor head retained therein according to one embodiment.

The embodiment illustrated in FIGS. 22-25 use a crown member 300 that is a separate member and that is insertable along with the anchor member 118 at the time of assembly. In embodiments shown in FIGS. 26A-B and 27A-B, the crown element 400, 500 is incorporated into the lower portion 234, 334 of the pivoting head 210, 310, respectively. With this alternative approach, the crown is not separately assembled. For example, FIGS. 26A and 26B depict a pivoting head 210 within which an anchor member 118 is retained. The anchor member 118 may be retained by deforming the head as described above or using retaining hardware such as a clip or ring. The crown member 400 is incorporated into the lower portion 234 of the pivoting head 210. More particularly, the crown 400 is joined to the lower portion 234 of the pivoting head 210 at attachment points 215. The attachment points 215 extend outward from the perimeter wall 239 of the crown 400 and inward from the wall forming the opening 226 in the pivoting head 210. In the illustrated embodiment, the crown 400 is suspended between the arms 220 that form the upper portion 216 of the pivoting head 210.

In the present embodiment, the crown 400 and the associated attachment points 215 are elastically deflectable in the direction of a downward force L that is applied when a rod 28 (not shown) is seated and secured within the upper saddle 216. The amount of deflection may be controlled in a variety of ways to vary the clamping force imparted on the anchor member 118 by the crown 400. The clamping force may be adjusted or selected as needed to produce a desired pivoting resistance for the anchor member 118. For instance, the thickness of the attachment points 215 may be varied such that the downward force L induces greater or lesser amounts of deflection. The choice of material for the pivoting head 210 will also affect the stiffness of the crown 400. Those skilled in the art will appreciate that a fatigue, load, and creep analysis may be appropriate to determined the long-term sustainability of the clamping force.

In one embodiment, the deflection illustrated in FIG. 26B includes at least some degree of plastic deformation. That is, the crown 400 may bend into the deflected state, and remain in that state even when the downward force L is removed. Despite this plastic deformation, the crown 400 may continue to perform its intended function of clamping the anchor member 118.

Figure 27A:
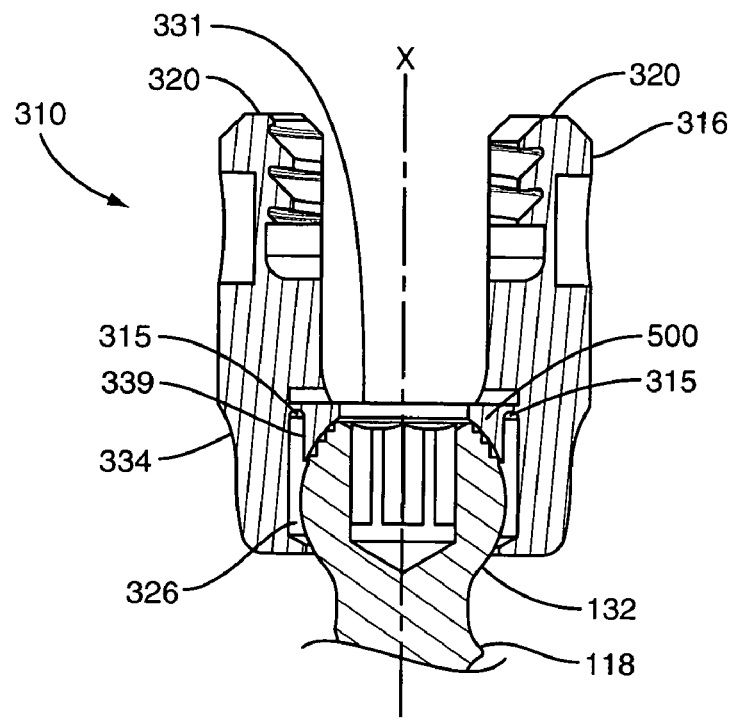
FIGS. 27A and 27B are side section views of a pivoting head with a detachable crown member and anchor head retained therein according to one embodiment.
Figure 27B:
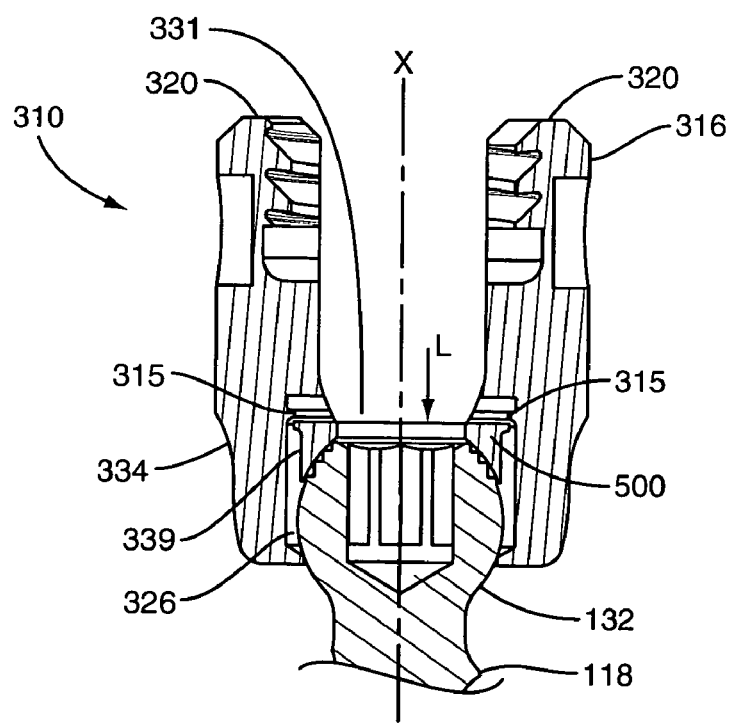

FIGS. 27A and 27B also depict an embodiment of a pivoting head 310 within which an anchor member 118 is retained. Similar to the embodiment shown in FIGS. 26A and 26B, the crown member 500 is incorporated into the lower portion 334 of the pivoting head 310. More particularly, the crown 500 is joined to the lower portion 334 of the pivoting head 310 at attachment points 315. The attachment points 315 extend outward from the perimeter wall 339 of the crown 500 and inward from the wall forming the opening 326 in the pivoting head 310. In the illustrated embodiment, the crown 500 is suspended between the arms 320 that form the upper portion 316 of the pivoting head 310.

In contrast with the embodiment shown in FIGS. 26A and 26B, the crown 500 in the present embodiment is detachable from the pivoting head 310 under the influence of a downward force L that is applied when a rod 28 (not shown) is seated and secured within the upper saddle 316. The attachment points 315 are configured to yield when the downward force L is applied. Yielding may be achieved with attachment points 315 that include a thin cross section, a perforated cross-section, notches, bends, or other mechanism to promote yielding. The yielding may be in the nature of plastic deformation or complete separation of the crown 500 from the pivoting head 310. FIG. 27B shows the latter type of yielding where the crown 500 has separated from the original attachment points 315 due to the application of the downward force L. With the crown 500 removed, a securing member 12 (not shown) may impart a clamping force onto a rod 28, which in turn, compresses the crown 500 between the rod 28 and the anchor head 132 to secure or limit the pivoting movement of the anchor member 118.

For the various embodiments described above, FIGS. 28A-28D depict exemplary process steps that may be used to retain the anchor member 18, 118 to the pivoting head 10, 110, 210, 310. To illustrate the process, the embodiment illustrated in FIGS. 22-25 is shown. It should be understood that other embodiments, including those illustrated in FIGS. 2-11, 18, 20, 21, and 26-27 may be formed using the illustrated process steps. In a first step shown in FIG. 28A, the pivoting head 110 is positioned into a holding fixture 600. The fixture 600 is depicted as a pair of opposed jaws, but other types of fixtures, including a chuck, a vise, a clamp, or other device known in the art may be used. The fixture 600 is adjusted as shown in FIG. 28B to secure the pivoting head 110. Once secured, the crown 300 is inserted into the cavity 126. In other embodiments, a wear member 30 may be inserted at this process step in lieu of the illustrated crown 300. In other embodiment, the crown 400, 500 is formed as a part of the pivoting head 210, 310 and is already positioned as desired.

Next, the anchor member 118 (or 18 in other embodiments) is inserted into the pivoting head 110. Then, as FIG. 28C depicts, a forming head 610 is brought into contact with the portion of the pivoting head 110 to be deformed. In the present example, the lower lip 156 is deformed under the influence of a deforming pressure P applied through the forming head 610. The pivoting head 110, the forming head 610, or some combination thereof may be rotated while the deforming pressure P is applied to the lower lip 156. The lower lip 156 is thereby deformed to the position shown in FIG. 28D to retain the retain the anchor member 118 within the pivoting head 110.

The process steps shown in FIGS. 28A-28D depict an exemplary forming process often referred to as orbital forming. It should be understood that other known manufacturing processes may be used to deform the pivoting head 10, 110 to retain the anchor member 18, 118. Some exemplary processes that may be used to achieve the desired deformation may include pressing, rolling, forging, swaging, staking, and stamping. Those skilled in the art will comprehend other manufacturing techniques that may be used to effectively captivate the anchor member 18, 118 as desired.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For example, embodiments described above have contemplated a pivoting head 10 having a substantially U-shaped recess in which to hold a longitudinal member 15. Certainly other types of configurations may incorporate the articulation mechanism 40 described herein. For example, alternative embodiments of the pivoting head may have circular apertures, C-shaped clamps, and multi-piece clamps as are known to secure a longitudinal member. The present embodiments are, therefore, to be considered in all respects as illustrative and not restrictive, and all changes coming within the meaning and equivalency range of the appended claims are intended to be embraced therein.

What is claimed is:

1. A method of connecting a vertebral anchor to a body that receives a longitudinal rod, the method comprising the steps of:
    pivotally attaching the vertebral anchor to the body by inserting a head of the vertebral anchor into an inlet of a cavity in the body and moving the head up towards an upper end of the cavity away from the inlet and towards a channel that receives the longitudinal rod;
    applying a force to walls of the body that form the cavity; and
    deforming the walls inward towards the vertebral anchor by orbital forming and reducing the width of the inlet from a first size that allows the head of the vertebral anchor to enter the cavity from outside the body to a second size that retains the head of the vertebral anchor within the cavity.

2. The method of claim 1 wherein the step of positioning the head of the vertebral anchor within the cavity in the body further comprises placing the head of the vertebral anchor within a receiving area of a compression member that is sized to fit within the cavity.

3. The method of claim 2 further comprising placing the head of the vertebral anchor within the receiving area of the compression member prior to positioning the head of the vertebral anchor and the compression member within the cavity in the body.

4. The method of claim 2 wherein the longitudinal rod contacts the compression member when the longitudinal rod is secured within the channel by a retaining member.

5. The method of claim 2 wherein the longitudinal rod is separated from the compression member when the longitudinal rod is secured within the channel by a retaining member.

6. The method of claim 2 further comprising inserting the compression member into the cavity prior to the step of positioning the head of the vertebral anchor within the receiving area, 7. The method of claim 2 wherein the compression member is formed as a part of the body.

8. The method of claim 1 further comprising securing the body in a holding fixture prior to deforming the body to retain the head of the vertebral anchor within the body.

9. A method of connecting a vertebral anchor to a body that receives a longitudinal rod, the method comprising the steps of:
    securing the body in a holding fixture, the body including a first end including a channel to receive the longitudinal rod and a second end including an inlet that leads into a cavity in the body, the cavity further including an upper end opposite from the inlet and a longitudinal axis that extends through the first and second ends;
    positioning a compression member into the cavity, the compression member including a smaller width than the cavity to move along the longitudinal axis;
    inserting a head of the vertebral anchor into the inlet of the cavity with the compression member positioned between the head and the upper end of the cavity;
    while the head of the vertebral anchor and the compression member are in the cavity, deforming the second end of the body and reducing the width of the inlet while maintaining the width of the upper end and capturing the head and the compression member in the cavity with the compression member and the head movable along the longitudinal axis.

* * * * *

UNITED STATES PATENT AND TRADEMARK OFFICE
CERTIFICATE OF CORRECTION

| | | |
|---|---|---|
| PATENT NO. | : 7,833,252 B2 | Page 1 of 1 |
| APPLICATION NO. | : 11/493447 | |
| DATED | : November 16, 2010 | |
| INVENTOR(S) | : Justis et al. | |

It is certified that error appears in the above-identified patent and that said Letters Patent is hereby corrected as shown below:

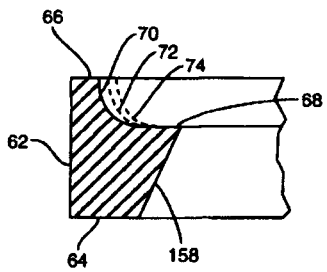

FIG. 15

After Fig. 14, Sheet 9 of 16, insert omitted Fig. 15 -- --.

In Column 6, Line 43, after "as well." delete "Further,".

In Column 11, Line 45, delete "determined" and insert -- determine --, therefor.

In Column 14, Line 15, in Claim 6, delete "area," and insert -- area. --, therefor.

Signed and Sealed this
Seventeenth Day of May, 2011

David J. Kappos
*Director of the United States Patent and Trademark Office*